(12) United States Patent
Reynolds et al.

(10) Patent No.: US 11,883,807 B2
(45) Date of Patent: Jan. 30, 2024

(54) FUNCTIONALIZATION OF METAL-ORGANIC FRAMEWORKS

(71) Applicant: Colorado State University Research Foundation, Fort Collins, CO (US)

(72) Inventors: Melissa M. Reynolds, Fort Collins, CO (US); Heather Rubin, Fort Collins, CO (US)

(73) Assignee: Colorado State University Research Foundation, Fort Collins, CO (US)

(*) Notice: Subject to any disclaimer, the term of this patent is extended or adjusted under 35 U.S.C. 154(b) by 408 days.

(21) Appl. No.: 16/500,243

(22) PCT Filed: Apr. 11, 2018

(86) PCT No.: PCT/US2018/027167
§ 371 (c)(1),
(2) Date: Oct. 2, 2019

(87) PCT Pub. No.: WO2018/191415
PCT Pub. Date: Oct. 18, 2018

(65) Prior Publication Data
US 2021/0114011 A1    Apr. 22, 2021

Related U.S. Application Data

(60) Provisional application No. 62/484,245, filed on Apr. 11, 2017.

(51) Int. Cl.
*B01J 31/00*    (2006.01)
*B01J 31/16*    (2006.01)
(Continued)

(52) U.S. Cl.
CPC ....... *B01J 31/1691* (2013.01); *B01J 31/2239* (2013.01); *D06M 16/00* (2013.01); *B01J 2531/0219* (2013.01); *B01J 2531/16* (2013.01)

(58) Field of Classification Search
None
See application file for complete search history.

(56) References Cited

U.S. PATENT DOCUMENTS

| | | | |
|---|---|---|---|
| 5,648,508 | A | 7/1997 | Yaghi |
| 5,691,423 | A | 11/1997 | Smith et al. |

(Continued)

FOREIGN PATENT DOCUMENTS

| | | | |
|---|---|---|---|
| EP | 2083946 | B1 | 8/2009 |
| EP | 2678041 | A2 | 1/2014 |

(Continued)

OTHER PUBLICATIONS

Cohen et al. JACS, 2010, 132, 4560-4561 (Year: 2010).*

(Continued)

*Primary Examiner* — Yun Qian
(74) *Attorney, Agent, or Firm* — Faegre Drinker Biddle & Reath LLP

(57) ABSTRACT

In some embodiments, a metal-organic framework material includes tricarboxylate metal-organic frameworks. The tricarboxylate metal-organic frameworks include unmodified tricarboxylate ligands and modified tricarboxylate ligands. The modified tricarboxylate ligands are unmodified tricarboxylate ligand modified with aliphatic carbon chains. Methods of forming metal-organic framework materials and textiles containing modified metal-organic framework materials are also provided.

4 Claims, 12 Drawing Sheets

(51) Int. Cl.
   *B01J 31/22*     (2006.01)
   *D06M 16/00*     (2006.01)

(56) References Cited

U.S. PATENT DOCUMENTS

| | | | |
|---|---|---|---|
| 6,451,337 | B1 | 9/2002 | Smith et al. |
| 6,887,485 | B2 | 5/2005 | Fitzhugh et al. |
| 7,087,709 | B2 | 8/2006 | Stamler et al. |
| 7,128,904 | B2 | 10/2006 | Batchelor et al. |
| 7,335,383 | B2 | 2/2008 | Meyerhoff et al. |
| 7,425,218 | B2 | 9/2008 | Keefer et al. |
| 7,637,983 | B1 | 12/2009 | Liu et al. |
| 7,763,283 | B2 | 7/2010 | Batchelor et al. |
| 7,829,553 | B2 | 11/2010 | Arnold et al. |
| 8,007,857 | B1 | 8/2011 | Hossainy |
| 8,771,756 | B2 | 7/2014 | Reynolds et al. |
| 8,907,043 | B2 | 12/2014 | James et al. |
| 9,034,355 | B2 | 5/2015 | Reynolds et al. |
| 9,493,352 | B2 | 11/2016 | Reynolds et al. |
| 2004/0087510 | A1 | 5/2004 | Garvey et al. |
| 2004/0224868 | A1 | 11/2004 | Meyerhoff et al. |
| 2005/0220756 | A1 | 10/2005 | Stamler et al. |
| 2005/0221072 | A1 | 10/2005 | Dubrow et al. |
| 2005/0265958 | A1 | 12/2005 | West et al. |
| 2006/0153795 | A1 | 7/2006 | West et al. |
| 2008/0069863 | A1 | 3/2008 | Peters |
| 2008/0220048 | A1 | 9/2008 | Chen et al. |
| 2008/0226686 | A1 | 9/2008 | Meyerhoff et al. |
| 2008/0255101 | A1 | 10/2008 | Garvey et al. |
| 2008/0306012 | A1 | 12/2008 | Hrabie et al. |
| 2009/0081279 | A1 | 3/2009 | Jezek et al. |
| 2009/0118819 | A1 | 5/2009 | Merz et al. |
| 2010/0285100 | A1 | 11/2010 | Balkus et al. |
| 2011/0159116 | A1 | 6/2011 | Reynolds et al. |
| 2014/0017121 | A1 | 1/2014 | Schoenfisch et al. |
| 2014/0178504 | A1 | 6/2014 | Reynolds et al. |
| 2015/0004257 | A1 | 1/2015 | Reynolds et al. |
| 2015/0118268 | A1 | 4/2015 | Reynolds et al. |
| 2015/0164821 | A1 | 6/2015 | McLaurin |
| 2016/0089444 | A1 | 3/2016 | Reynolds et al. |
| 2017/0028390 | A1* | 2/2017 | Reynolds ............ B01J 20/3212 |
| 2021/0169082 | A1 | 6/2021 | Reynolds et al. |

FOREIGN PATENT DOCUMENTS

| | | |
|---|---|---|
| EP | 3651580 A1 | 5/2020 |
| FR | 2929278 A1 | 10/2009 |
| WO | 03/60003 A1 | 7/2003 |
| WO | 2008020218 A1 | 2/2008 |
| WO | 2008062160 A1 | 5/2008 |
| WO | 2012116177 A2 | 8/2012 |
| WO | 2013/006458 A1 | 1/2013 |
| WO | 2013138073 A1 | 9/2013 |

OTHER PUBLICATIONS

Cohen et al. JACS, 2010, 132, 4560-4561, and Supporting Information (Year: 2010).*

Oh, B. K. et al., "Spontaneous Catalytic Generation of Nitric Oxide from S-Nitrosothiols at the Surface of Polymer Films Doped with Lipophilic Copper(II) Complex", Journal of the American Chemical Society, 2003, 125, 9552-9553.

Palmer, R.M.J. et al., "Vascular endothelial cells synthesize nitric oxide from L-arginine", Nature, vol. 333, Jun. 16, 1988, pp. 664-666.

Parola, S., et al. (2016). Optical Properties of Hybrid Organic-Inorganic Materials and their Applications. Adv. Funct. Mater., 26:6506-6544.

Prakash, M. Jaya et al., "Metal-organic macrocycles, metal-organic polyhedra and metal organic frameworks", Chem. Commun., 2009, 3326-3341.

Puiu, S. C. et al., "Metal Ion-Mediated Nitric Oxide Generation From Polyurethanes via Covalently linked CopperII Cyclen Moieties", Journal of Biomedical Materials Research Part B Applied Biomaterials, 2009, 203-212.

Qiu, Shilun et al., "Molecular engineering for synthesizing novel structures of metal-organic frameworks with multifunctional properties", Coordination Chemistry Reviews 253 (2009) 2891-2911.

Schlichte, K. et al., Improved Synthesis, thermal stability and catalytic properties of the metal organic framework compound Cu3BTC2, Micropourous and Mesoporous Materials, 2004, 73, 81-88.

Seabra, Amedea B. et al., "Nitric Oxcide-Releasing vehicles for Biomedical Applications", Journal of Materials Chemistry, published 2010, 20, pp. 1624-1637.

Shah, S. U., et. al. Synthesis and Characterization of S-Nitrosoglutathione-Oligosaccharide-Chitosan as a Nitric Oxide Donor. Expert Opinion on Drug Delivery, 12(8):1209-1223, Mar. 24, 2015.

Shin et al. Improving the biocompatibility of in vivo sensors via nitric oxide release, The Analyst, 2006, 131, pp. 609-615.

Smith, D. J. et al., "Nitric Oxide releasing polymers Containing the NONO Group", Journal of Medicinal Chemistry, 1999, 39, 1148-1156.

Soni, S. D., et. al. Nitric Oxide-Releasing Polymeric Microspheres Improve Diabetes-Related Erectile Dysfunction. J. Sex. Med., 10:1915-1925, 2013.

Tanabe, K. K. et al., "Systematic Functionalization of a Metal Organic Framework via a Postsynthetic Modification Approach", Journal of the American Chemical Society, 2008, 130, 8508-8517.

Third Party Observations issued in EP Application No. 10 80 3195.6, mailed Jul. 13, 2015, 3 pages.

Trafton, Anne; Nitric Oxide shown to cause colon cancer, MIT News, 2009, (http://newsoffice.mit.edu/2009/colon-cancer-0119).

Wang, Z. et al., "Post Synthetic Modification of Metal Organic Frameworks", Chemical Society Reviews, 2009, 38, 1315-1329.

Williams, L. H. et al., "The Chemistry of S-Nitrosothiols", Accounts of Chemical Research, 1999, 32, 869-876.

Xiao, Bo et al., "High Capacity Hydrogen and Nitric Oxcide Adsorption and Storage in a Metal-Organic Framework", Journal American Chemical Society, vol. 129, No. 5, 2007, pp. 1203-1209.

Xiao, Bo et al., "High-Capacity Hydrogen and Nitric Oxide Adsorption and Storage in a Metal Organic Framework", Journal of the American Chemical Society, American Chemical Society, US, vol. 129, No. 5, Feb. 7, 2007, pp. 1203-1209.

Yaghi, O. M. et al., "Reticular Synthesis and the Design of new Materials", Nature 2003, vol. 423, pp. 705-714.

Yaghi, O. M. et al., "Synthetic Strategies, Structure Patterns, and Emerging Properties in the Chemistry of Modular Porous Solids", Accounts of Chemical Research 1998, vol. 31 No. 8, pp. 474-484.

Abdelhameed, R. M. (2014). Post-synthetic modification of metal-organic frameworks. University of Aveiro, Department of Chemistry, 232 pages.

Allendorf, Mark D. et al., "Plasmonic Devices and Sensors Built from Ordered Nanoporous Materials", Sandia Report, SAND2009-5964, Unlimited Release, Printed Sep. 2009, Sandia National Laboratories, 40 pages.

Alsadoni, H. H., "S-Nitrosothiols as Nitric Oxide-Donors: Chemistry, Biology and Possible Future Theraputic Applications", Current Medicinal Chemistry 2004, 11, 2679-2690.

Askew, S. C. et al., "Catalysis by Cu2+ of nitric oxide release from S-nitrosothiols (RSNO)", Journal of the Chemical Society Perkin Transaction 2, 1995, 8, 741-745.

Bordiga, S. et al., "Adsorption Properties of HKUST-1 Toward Hydrogen and Other Small Molecules Monitored by IR", Physical Chemistry Physics, vol. 9, 2007, pp. 2676-2685.

Britt, David et al., "Ring-Opening Reactions Within Porous metal-Organic Frameworks", Inorg. Chem. 2010, 49, 6387-6389.

Chen, Banglin et al., "A Microporous Metal-organic Framework for Gas-Chromatographic Separation of Alkanes", Angew. Chem. 2006, 118, pp. 1418-1421.

Chui, S. et al., "A Chemically Functionalizable Nanoporous Material Cu3TMA2H2O3", Science 1999, vol. 283, pp. 1149-1150.

Dahm, Christina C.; et al. "Persistent S-Nitrosation of Complex I and Other Mitochondrial Membrane Proteins by S-Nitrosothiols but

(56) References Cited

OTHER PUBLICATIONS

Not Nitric Oxide or Peroxynitrite." Journal of Biological Chemistry, 281(15):10056-10065, Apr. 14, 2006.

Damodaran, Vinod Babu et al., "Conformational Studies of Covalently Grafted Poly(ethylene Glycol) on Modified Solid Matrices Using X-ray Photoelectron Spectroscopy", Langmuir 2010, vol. 26, No. 10, pp. 7299-7306.

Demessence, A. et al., "Strong CO2 Binding in a Water-Stable, Triazolate-Bridged Metala Organic Framework Functionalized with Ethylenediamine", Journal of the American Chemical Society, 2009, 131 (25), 8784-8786.

Dicks, A. P. et al., "Decomposition of S-nitrosothiols: the effects of added thiols", Journal of the Chemical Society Perkin Transactions 1997, pp. 1429-1434.

Dicks, A. P. et al., "Generation of nitric oxide from S-nitrosothiols using protein bound Cu2+ sources", Chemistry & Biology 1996, vol. 3, 655-659.

Dicks, Andrew P. et al., "Identification of Cu as the effective reagent in nitric oxide formation from S-nitrosothiols (RSNO)", J. Chem. Soc., Perkin Trans. 2, 1996, pp. 481-487.

Dinca et al., Observation of Cu2—H2 Interactions in a Fully Desolvated Sodalite-Type Metal-Organic Framework, Angewandte Chem., Int. Ed., 2007, 46, pp. 1419-1422.

Drago, R. S. et al., "The Reaction of Nitrogen (II) Oxide with Diethylamine", Journal of the American Chemical Society, 1960, 82, 96-98.

Drago, R.S. et al., "The Reaction of Nitrogen (II) Oxide with Various Primary and Secondary Amines", Journal of the American Chemical Society, 1961, 83, 1819-1822.

Eddaoudi, M. et al., "Modular Chemistry: Secondary Building Units as a Basis for the Design of Highly Porous and Robust Metal Organic Carboxylate Frameworks", Acc. Chem. Res., 2001, 34, 319-330.

Ellman, George L., "Tissue Sulfhydryl Groups", Archives of Biochemistry and Biophysics vol. 83, 70-77 (1959).

Ene, Cristian D. et al., "One-dimensional and two-dimensional coordination polymers constructed from copper(II) nodes and polycarboxylato spacers: synthesis, crystal structures and magnetic properties", Polyhedron 27(2008) 574-582.

Extended European Search Report issued in EP Application No. 12749029.0, dated Nov. 19, 2015, 11 pages.

Fleser, P. S. et al., "Nitric oxide-releasing biopolymers inhibit thrombus formation in a sheep model of arteriovenous bridge grafts", Journal of Vascular Surgery 2004, vol. 40 No. 4, 803-811.

Frost, M. C. et al., "Polymers Incorporating Nitic Oxide Releasing/Generating Substances for Improved Biocompatibility of Blood-Contacting Medical Devices", Biomaterials 2005, 26, 1685-1693.

Frost, Megan C. et al., "Synthesis, Characterization, and Controlled Nitric Oxide Release from S-Nitrosothiol-Derivatized Fumed Silica Polymer Filler Particles", Copyright 2005, Wiley Periodicals, Inc., pp. 409-419.

Furuyama, Shozo et al., "Physisorption of Nitric Oxide, Carbon Monoxide, Nitrogen, and Oxygen by Magnesium Oxide Powder", The Journal of Physical Chemistry, vol. 28, No. 9, 1978, pp. 1028-1032.

Garibay, Sergio J. et al., "Postsynthetic Modification: A Versatile Approach Toward Multifunctional Metal-Organic Frameworks", Inorg. Chem. 2009, 48,7341-7349.

Harding, Jacqueline L. et al., "Metal Organic Frameworks as Nitric Oxide catalysts", J. Am. Chem. Soc. 2012, 134(7), pp. 3330-3333.

Hart, T. W., "Some Observations Concerning the S-nitroso and S-phenylsulphonyl Derivatives of L-cysteine and Glutathione", Tetrahedron Letters 1985, 26 (16), 2013-2016.

Herm, Zoey R. et al., "Metal-Organic Frameworks as Adsorbents for Hydrogen Purification and Precombustion Carbon Dioxide Capture", Journal of the American Chemical Society, Mar. 25, 2011, No. 133, pp. 5664-5667.

Herm, Zoey R. et al., "Metal-Organic Frameworks as Adsorbents for Hydrogen purification and precombustion Carbon Dioxide Capture", Journal of the American Chemical Society, 2011, vol. 133, pp. 5664-5667.

Horcajada, P., et al. (2006). Metal-Organic Frameworks as Efficient Materials for Drug Delivery. Angew. Chem. Int. Ed., 45:5974-5978.

Hrabie, J. A. et al., "New Nitric Oxide Releasing Zwitterions Derived from Polyamines", Journal of Organic Chemistry 1993, 58, 1472-1476.

http://www.plasticfantasticlibrary.com/library/plastic/156/polyoxybenzylmethylenglycolanhydride.html,"Plastic Fantastic Library Entry for polyoxybenzylmethylenglycolanhydride (Bakelite)" Accessed Aug. 1, 2018, no pagination.

Ignarro, Louis J. et al., "Nitric Oxide Donors and Cardiovascular Agents Modulating the Bioactivity of Nitric Oxcide: An Overview", Cirrulation Research, Jan. 2002, 90, pp. 21-28.

Ingleson, Michael J. et al., "Nitric Oxide Chemisorption in a Postsynthetically Modified metal-Organic Framework", Inorg. Chem. 2009, 48, 9986-9988.

International Preliminary Report on Patentability issued in PCT/US2012/026317, completed Mar. 18, 2014, 6 pages.

International Preliminary Report on Patentability issued in PCT/US2018/027167, dated Oct. 24, 2019, 10 pages.

International Search Report and Written Opinion issued in PCT/US2010/062229, dated Apr. 15, 2011, 9 pages.

International Search Report and Written Opinion issued in PCT/US2012/026317 dated Dec. 6, 2012, 10 pages.

International Search Report and Written Opinion issued in PCT/US2012/026317, dated Jun. 6, 2012, 10 pages.

International Search Report and Written Opinion issued in PCT/US2018/027167, dated Jul. 6, 2018, 12 pages.

Isaeva, V.I. et al., "The Application of Metal-Organic Frameworks in Catalysis (Review)", Petroleum Chemistry, 2010, vol. 50, No. 3, pp. 167-180.

James, S. L. et al. et al., "Metal Organic frameworks", Chemical Society Reviews, 2003, 32, 276-288.

Kitagawa, Susumu et al., "Functional Porous Coordination Polymers", Angew. Chem. int. Ed. 2004, 43, 2334-2375.

Li, H. et al., "Design and Sythesis of an exceptionally stable and highly porous metal organic framework", Nature 1999, vol. 402, pp. 276-279.

Liu et al. "Preparation and characterization of an improved Cu2+-cyclen polyurethane material that catalyzes generation of nitric oxide from S-nitrosothiols", J Mater Chem. Jan. 1, 2012; 22(36): 18784-18787.

McKinlay, Alistair C. et al., "Exceptional Behavior over the Whole Adsorption—Storage—Delivery Cycle for NO in Porous Metal Organic Frameworks", J. Am. Chem. Soc. 2008, 130, 10440-10444.

McKinlay, Alistair C. et al., "Exceptional Behavior Over the Whole Adsorption Storage Delivery cycle for NO in Porous Metal Organic Frameworks", Journal of the American Chemical Society, vol. 130, 2008, pp. 10440-10444.

Nguyen, J. G. et al., "Moisture-Resitant and Superhydrophobic Metal-Organic Frameworks Obtained via Postsynthetic Modification", Journal of the American Chemical Society, 2010, 132, 4560-4561.

Noble, D. R. et al., "Structure Reactivity Studies of the Cu2 plus catalyzed Decomposition of Four S Nitrosothiols Based around the S NitrocysteineS Nitrosoglutathione Structures", Nitric Oxide: Biology and Chemistry, 2000, 4 (4), 392-398.

Andrew L. Hook et al., "Discovery of Novel Materials with Broad Resistance to Bacterial Attachment Using Combinatorial Polymer Microarrays", Advanced Materials 2013, 25, pp. 2542-2547, wileyonlinelibrary.com.

International Preliminary Report on Patentability issued in PCT/US2018/041644, dated Jan. 23, 2020, 6 pages.

International Search Report and Written Opinion issued in PCT_US 18_41644, dated Oct. 30, 2018, 11 Pages.

Neufeld et al. "Metal-Organic Framework Material Inhibits Biofilm Formation of Pseudomonas aeruginosa" Advanced Functional Materials. Sep. 13, 2017 (Sep. 13, 2017) vol. 27; pp. 1-9.

Neufeld et al. "Metal-Organic Framework/Chitosan Hybrid Materials Promote Nitric Oxide Release from S-Nitrosoglutathione in

(56) References Cited

OTHER PUBLICATIONS

Aqueous Solution" ACS Applied Materials & Interfaces. Feb. 2, 2017 (Feb. 2, 2017) vol. 9, p. 5139-5148; p. 5139, abstract, left col, para 1, p. 5140. left col, para 1, right col, para 1, p. 5142, left col, para 4, p. 6143, left col, para 1, p. 5145, right col, para 3.

Harding et al., "A tunable, stable and bioactive MOF catalyst for generating a localized therapeutic from endogenous sources", Adv. Func. Mater., vol. 24, 2014, pp. 7503-7509.

Lu et al. (ACS Appl. Mater. Interfaces 2016, 8, 16533-16539). (Year: 2016).

Mekahlia et al., "Chitosan-Copper (II) complex as antibacterial agent: synthesis, characterization and coordinating bond-activity correlation study", Physics Procedia, vol. 2, No. 3, 2009, pp. 1045-1053.

* cited by examiner

… …

FUNCTIONALIZATION OF METAL-ORGANIC FRAMEWORKS

CROSS-REFERENCE TO RELATED APPLICATION

This application is a U.S. 371 National Stage Application of International Application No. PCT/US2018/027167, filed Apr. 11, 2018, which claims priority to U.S. Provisional Application No. 62/484,245, filed Apr. 11, 2017, both of which are herein incorporated by reference in their entireties.

STATEMENT REGARDING FEDERALLY SPONSORED RESEARCH OR DEVELOPMENT

This invention was made with government support under a NSF CAREER Award (award number 1352201) awarded by the National Science Foundation. The government may certain rights in the invention.

BACKGROUND

The ability to predictably tune the properties of a material expands its overall usefulness, leading to enhanced functionality for target-specific applications. Hybrid materials are comprised of two or more constituents and inherently possess a high degree of tunability attributable to the ability to manipulate each individual component. Metal-organic frameworks (MOFs) are a distinct class of organic-inorganic hybrid nanomaterials consisting of tunable coordination networks. Manipulation at either the metal ion centers, the organic linkers, or both, yields seemingly infinite possibilities to control the physicochemical properties of the materials.

One such framework, copper benzene-1,3,5-tricarboxylate ($Cu_3(BTC)_2$), has shown a range of notable applications; however, water instability presents a significant obstacle for practical use. A method to control the interaction of a MOF with water would permit this instability to be circumvented or exploited for a specific application.

Nano-antimicrobial materials offer the unique opportunity to fill the void associated with current antibiotic treatment failure. The development of antibacterial surfaces to prevent the spread and growth of bacteria remains a materials necessity of high priority to combat a pressing global health concern. Bacteria may thrive for weeks to months upon common surfaces including bandages, clothing, and blankets. Once materials of this type are compromised with microbial attachment, it is likely for the bacteria to advance to biofilm formation, whereby microbial cells become increasingly impenetrable to traditional antibiotics, making treatment extremely difficult. An optimal strategy is to develop efficient antimicrobial coatings, metals, and fabric materials which kill or prevent the attachment of bacteria altogether. Using small molecules which kill bacteria via multiple mechanisms is a relatively well-established route with excellent success rates to avoid bacterial resistance. On the other hand, it is easier to prevent than treat biofilms. Thus, materials with surfaces that prevent the attachment of bacteria altogether would minimize the spread of bacteria and in turn lessen the necessity for traditional antibiotics. Towards this goal, antimicrobial materials, which kill or inhibit the growth of microorganisms have become a centralized focus for materials science.

While traditional antibiotics target inhibition of DNA replication, cell wall synthesis, or protein synthesis, all of which primarily due to resultant secondary oxidative species, materials containing nanoparticles, on the other hand, are suspected to be unaffected by most resistance mechanisms as they display multiple modes of action. This includes the direct interaction of the nanoparticles with the bacterial cell membranes to kill bacteria and prevent biofilm formation, induce metal-redox species which causes oxidative stress to damage bacterial cell components, and disrupt critical permeability into or out of the cell. Nanomaterials also serve as excellent drug carriers, which would support and strengthen traditional antibiotic treatments. Moreover, release of small molecules or metal ions with antibacterial properties has shown promise for strategically developing antibacterial materials.

Under controlled conditions, copper ions have proven nontoxic and highly effective at killing bacteria and preventing the formation of biofilms. Copper containing MOFs, therefore, may present a promising opportunity to develop useful and effective antibacterial materials. While release of $Cu^{2+}$ ions has been observed with non-porous copper containing materials, manipulation of ion release rates is limited to the surface area of the material or specialized coatings.

SUMMARY

In some embodiments, a metal-organic framework material includes tricarboxylate metal-organic frameworks. The tricarboxylate metal-organic frameworks include unmodified tricarboxylate ligands and modified tricarboxylate ligands. The modified tricarboxylate ligands are unmodified tricarboxylate ligand modified with aliphatic carbon chains. The metal-organic framework material has at least 6% modification.

In some embodiments, a method of modifying tricarboxylate metal-organic frameworks includes contacting tricarboxylate metal-organic frameworks with a composition containing aliphatic carbon chains.

In some embodiments, a method for controlled modification of tricarboxylate metal-organic frameworks includes selecting an anhydride to produce modified tricarboxylate metal-organic frameworks having a determined water contact angle based on a determined relationship between a reference anhydride and a water contact angle for a reference modified tricarboxylate metal-organic framework; and exposing the selected anhydride in a determined equivalent amount to the tricarboxylate metal-organic frameworks to produce the modified tricarboxylate metal-organic frameworks having the determined water contact angle.

In some embodiments, method of forming a textile includes carboxymethylation of a surface of the textile; layer-by-layer growth of a tricarboxylate metal-organic framework film on the surface of the carboxymethylated surface; and forming a modified tricarboxylate metal-organic framework film by exposing the tricarboxylate metal-organic framework film to an anhydride.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Figure 1:
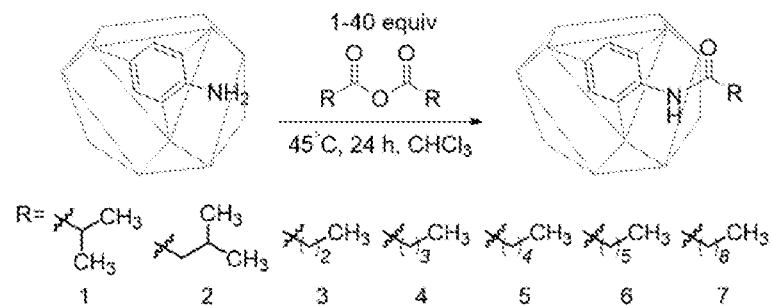
FIG. 1 is a schematic illustration of PSM of an exemplary MOF with various anhydrides.

Disclosed herein is a metal-organic framework (MOF) material containing MOFs that have been post-synthetically modified. More specifically, disclosed herein is a MOF material containing modified tricarboxylate ligands.

Metal-organic frameworks (MOFs) are a distinct class of organic-inorganic hybrid nanomaterials having metal ion centers and organic linkers or ligands. Copper benzene-1,3,5-tricarboxylate ($Cu_3(BTC)_2$) is used herein as one exemplary tricarboxylate MOF or MOF containing tricarboxylate ligands. $Cu_3(BTC)_2$ includes copper ion centers and tricarboxylate linkers or ligands. Other suitable tricarboxylate MOFs include Fe-BTC, $Cr_3(BTC)_2$, Zr(IV)—BTC, and $Zn_2(BTC)$.

The modified tricarboxylate MOFs disclosed herein include copper ion centers, unmodified tricarboxylate linkers and modified linkers. The modified linkers are tricarboxylate linkers modified with aliphatic carbon chains. The modified tricarboxylate MOFs have mixed-ligands. For example, the modified tricarboxylate MOFs can include unmodified tricarboxylate ligands and tricarboxylate ligands modified with a hydrocarbon. Suitable hydrocarbons include linear hydrocarbons and branched hydrocarbons. In some embodiments, the hydrocarbons may have any suitable chain length.

The degree of modification of the MOF material (the percent of modified linkers to total linkers of the modified MOF material) can be varied. A suitable amount of modification is the amount of modification necessary to change or improve a physical or chemical property of the MOF material. In some embodiments, MOF material having at least 6% modification exhibited improved hydrophobic properties.

In some embodiments, the MOFs are isoreticular to copper benzene-1,3,5-tricarboxylate ($Cu_3(BTC)_2$), the MOF material has at least 6% modification and less than 100% modification and the modified tricarboxylate ligands are modified with carbon lengths of 4 or more.

The modified metal-organic frameworks can be formed using a post-synthetic modification (PSM) process. The PSM provides a method of obtaining new physical and chemical characteristics with preexisting MOFs via late stage functionalization of the MOFs. In some embodiments, the PSM may occur when the MOF is in powder form. In other embodiments, the PSM may occur before or after the MOF is incorporated into a product. For example, the MOF may be incorporated onto a cellulose substrate and subsequently the PSM may be performed.

One PSM disclosed herein, the MOF is exposed to suitable aprotic solvent and a desired hydrocarbon source, such as an anhydride. Suitable aprotic solvents include chloroform ($CHCl_3$), dichoromethane, acetone, acetonitrile, diethyl ether, benzene, toluene. The source of the carbon chains should be soluble in a solvent and can be any electrophilic source of carbon. In some embodiments, the MOF may be dosed with 1, 10, 20 or 40 equivalents or any range thereof of the desired anhydride.

The resulting material contains modified MOFs having unmodified ligands and ligands modified with carbon chains from a suitable source, such as an anhydride. In one embodiment, $Cu_3(NH_2BTC)_2$ was exposed to $CHCl_3$ to produce a highly uniform, crystalline green powder that was subsequently functionalized with various anhydrides. This yielded a series of modified frameworks having mixed-ligands. The percent conversions or percentage of modification can be calculated by comparing the ratio of the aromatic chemical shifts associated with the unmodified and modified ligands in the $^1$H NMR spectra of each independent acid digested material.

Based on equivalents of anhydride to amine added, the percentage of modification is varied. In some embodiments, the MOF material was modified with 1, 10, 20 or 40 equivalents, regardless of whether the anhydride was branched or unbranched. Surprisingly, reliability and reproducibility to obtain mixed-ligands ratios was observed. Additionally, drastic changes in the hydrophobic character of the material were simultaneously achieved even at low conversion quantities.

Tricarboxylate ligands have an increased level of steric hindrance. It was previously thought that this steric hindrance may impede access to the functional handle intended for modification. As described herein, it was surprisingly found that $NH_2H_3BTC$ can be accessed with a scalable, cost-effective synthesis to provide a tricarboxylate MOF for PSM, and MOFs with sterically hindered constituents can undergo covalent PSM with long chained and branched hydrocarbons.

The covalent post-synthetic modification confers hydrophobicity to the MOF material. For example, unmodified $Cu_3(NH_2BTC)_2$ degrades in minutes upon contact with water, whereas modification as low as 14% results in powders that show significantly enhanced hydrophobicity with contact angles up to 147°. In some embodiments, the modified material exhibited hydrophobic to nearly superhydrophobic water contact angles (120-150°). The modified material is capable of withstanding direct contact with water for 30 minutes with no visual evidence of altered surface characteristics.

The covalent post-synthetic modification reduces sorption rates. For example, modifying $Cu_3(NH_2BTC)_2$ with a 7% conversion using valeric anhydride resulted in water sorption rates decreasing from 8.8 μL/sec to 0.46 μL/sec.

A linear relationship was observed between the length of the tethered chain of the anhydride and the water contact angle. This results in a predictable method for achieving a range of desirable sorption rates and controllable hydrophobic character. Rendering the modified material more stable in aqueous environments significantly impacts long-term applications. While changing the overall wettability of material from hydrophilic to hydrophobic is valuable, control over the degree of hydrophobicity expands the usefulness of the material.

Rendering the material more stable in aqueous environments significantly impacts long-term applications for the modified materials. Wettability is a characteristic that attracts significant attention in the practical applicability of materials. Engineering the wettability of a material presents a rational, yet complex solution to combat failure related to water absorptivity in biomedical, energy, environmental and industrial systems. The ability to carefully and predictably tune MOF wettability enhances potential applications and provides a material with controllable desired characteristics.

The covalent post-synthetic modification provides predicable tunable degradation rates, which holds potential for drug carriers with tunable drug release. For example, the anhydride and the degree of modification can be selected to achieve a desired degradation rate. The porosity achieved with MOFs gives these particular systems unique properties due to increased surface area-to-mass ratio over other nanomaterials. This characteristic effectively increases interactions with cells in biological mediums, adversely affecting bacterial cell membranes. The controlled release and decomposition kinetics of the modified MOF itself or guest molecules pre-loaded into the pores yields effective synergistic therapeutic delivery systems. As such, the modified MOFs disclosed herein are excellent candidates for incorporation into materials to achieve antibacterial activity.

As discussed herein, it was surprisingly found that there was a linear relationship between the length of the tethered chain of the anhydride and the water contact angle. In one embodiment, the anhydride and the amount of anhydride are selected to produce a MOF material having desired hydrophobic and/or degradation properties. For example, the linear relationship between the length of the tethered chain of an anhydride and the water contact angle for a given MOF can be determined by synthesizing modified MOFs and determining the water contact angle of each. In one embodiment, the water contact angle is determined by CAG. For each sample, the contact angle is plotted versus the number of carbons in the PSM amide modification. A line is fit to the data and the equation of the line is determined. For example, the data may have a linear fit with an equation of $y=Ax+B$. By inserting a desired number of carbons in the carbon chain length for x, one can solve for the observed contact angle, y. Alternatively, if a desired contact angle is inserted for y, an estimated number of carbons needed in the amide chain can be deduced by solving for x.

Based on the determined relationship, an anhydride can be selected and the appropriate equivalent amount of the selected anhydride can be calculated to produce modified MOFs having a desired or determined water contact angle based on determined relationship for the given MOF. In this way, modified MOF material having reliable, consistent, and predetermined physical and chemical properties can be produced.

In some embodiments, the modified tricarboxylate MOFs are incorporated onto a substrate. Suitable substrates include any substrate in which a surface of the substrate is capable of undergoing a chemical modification to incorporate an available carboxylate on to the surface. For example, suitable substrates include polymers and textiles or fabrics such as cellulose or cotton textiles. In some embodiments, the MOFs are incorporated onto the textile and are subsequently modified. For example, a copper MOF-cotton material is fabricated and PSM is used to introduce a free amine to modify or tune the properties of the material. The modified tricarboxylate MOF-textile material may have uniformly distributed MOF crystals around carboxymethylated fiber. For example, the modified tricarboxylate MOF-textile material can have uniformly distributed 1 μm by 1 μm octahedral MOF crystals around each carboxymethylated fiber.

In one embodiment, a copper MOF-cotton material is fabricated by carboxymethylation of cotton material, which enhance the numbers of nucleation sites for MOF growth. For example, to increase nucleation sites for the growth of the MOF, the appendant hydroxyl moieties of the cotton fabric can be modified to yield available carboxylates on the surface. The carboxymethylation can be selected so that the substrate is synthetically manipulated to provide a nucleation site which mimics that of the ligand within the desired MOF. In some embodiments, a cotton surface can be modified under basic conditions with sodium chloroacetate and sodium hydroxide. In some embodiments, the carboxymethylation uses a solution containing water and an alcohol, such as ethanol and/or isopropanol. It has been found that the addition of alcohol to the carboxymethylation solution yields a greater percentage of carboxylate moieties on the surface of the substrate.

Subsequently, the MOF, such as $Cu_3(NH_2BTC)_2$, is synthesized into a homogenous surface supported film by a layer-by-layer dip coating process on the modified material. For example, the resultant nucleation sites on the textile can enable the immobilization of the MOF chemically bound to the textile fibers by a layer-by-layer growth process by repetitively dipping the textile into alternating solutions of a copper source and a ligand source. For example, a suitable copper source solution may contain a copper (II) source such as copper nitrate, copper (II) acetate and copper (II) chloride. A suitable ligand source solution contains the desired ligand. In some embodiments, the suitable ligand has a free nucleophilic functional handle and include a free thiol or alcohol. In some embodiments, the ligand is $NH_2H_3BTC$. In some embodiments, the dipping process may be achieved using a mechanical dip coater.

The surface supported MOF film can then be exposed to an electrophilic source of carbon, such as an anhydride, for PSM as disclosed herein to form the modified tricarboxylate MOF-textile material. The accessible free-amine of the MOF ligand allowed for PSM of the MOF-cotton surface with an anhydride. In some embodiments, a MOF-cotton surface modified with valeric anhydride yielded 23.5±2.2% modification. The copper MOF-cotton material can be subject to a PSM as described herein resulting in improved physical and chemical properties including wettability, sorption and tunable degradation.

The modified tricarboxylate MOF-textile material releases $Cu^{2+}$ ions, for example under biological conditions which can be simulated by submersion in complex media at 37° C. It was found that PSM induces a change in the copper flux of the material over the first 6 hours. In some embodiments, the modified tricarboxylate MOF-textile material continues to slowly release $Cu^{2+}$ ions beyond the 24 hours at a flux of $0.25\pm0.004$ $\mu mols \cdot cm^{-2} \cdot h^{-1}$. In comparison, the same copper MOF-cotton material in an unmodified state had a flux of $0.22\pm0.003$ $\mu mols \cdot cm^{-2} \cdot h^{-1}$.

Tunable ion release is advantageous for various environmental and biomedical applications as it provides an opportunity to control ion delivery rates. By utilizing a ligand scaffold that contains a functional handle for post-synthetic modification (PSM) of the material, a MOF-system capable of releasing antibacterial agents is amenable to fine tuning. This offers the opportunity to manipulate the physicochemical properties of the materials, offering control over the stability to aqueous environments using late-stage synthetic functionalization.

The modified tricarboxylate MOF-textile material has antibacterial activity. In some embodiments, the antibacterial activity of the material can be demonstrated using *Escherichia coli* by testing the planktonic and attached bacteria under a variety of conditions. The modified tricarboxylate MOF-textile material can yield a log-4 reduction or greater after 24 hours of exposure. In some embodiments, the modified tricarboxylate MOF-textile material can inhibit the attachment of bacteria under dry conditions, wet conditions or both dry and wet conditions. Thus, the modified tricarboxylate MOF-textile material can be used to develop textile materials containing uniform, tunable modified MOF composites that can kill bacterial and/or prevent the attachment of bacteria to the surface of the textile.

Synthetically growing MOF crystals or films bound to the surface produces substantially uniform films with homogenous or substantially homogenous crystal formation. Previously, MOF coatings on surfaces often resulted in non-uniform coverage with heterogeneous crystal formation. The resultant polycrystallinity and/or inhomogeneity may interfere with the material's final performance leading to batch to batch inconsistencies.

The low temperatures associated with tricarboxylate MOF syntheses as compared to other copper containing synthetic processes, allows for MOF incorporation into more sensitive, flexible materials, like polymers and textiles. Such surfaces, including bandages, curtains, and garments all serve as proponents for bacteria to attach, proliferate, and spread. Potential applications of such textiles include medical supplies, apparel, and common fabrics.

EXPERIMENTAL SECTION

Materials.

Anhydrous dimethylformamide (DMA), anhydrous chloroform ($CHCl_3$), dimethylsulfoxide (DMSO), sodium hydroxide, and copper (II) nitrate, and anhydrous methanol (MeOH) were purchased through Sigma Aldrich. $Cu_3(BTC)_2$ was purchased as Basolite C300 from Sigma Aldrich. Absolute ethanol was attained via Pharmco-Aaper. Deuterium chloride (DCl) was purchased from Acros Organics. Anhydrides were purchased from TCI. Natural resized and bleached cotton was purchased via SDL Atlas. Sodium chloroacetate was purchased through Ark Pharm Inc. All materials were used as provided, without further purification. Oxoid™ nutrient broth media (NBM, OXCM0001B), Oxoid™ nutrient agar (NA, OXCM0003B), and sodium chloride were purchased from Fisher Scientific. *Escherichia coli* (*E. coli*, ATCC 25922) was purchased from the American Type Culture Collection (ATCC). The synthesis of the MOF herein is previously described in the literature (see Liu, Y.; Suo, X.; Wang, Z.; Gong, Y.; Wang, X.; Li, H. Developing Polyimide-Copper Antifouling Coatings with Capsule Structures for Sustainable Release of Copper. *Mater. Des.* 2017, 130, 285-293). A Millipore purification system set at 18 MΩ was used for all water submersion experiments. Syntheses sensitive to air and moisture were performed using standard Schlenk techniques under an atmosphere of inert nitrogen or argon.

Characterization.

All NMR experiments were performed using an Agilent (Varian) 400MR equipped with automated tuning and a 7600 sample changer at room temperature. All NMR spectra were analyzed using MestReNova NMR software. In order to verify and quantify modification to each ligand after the above PSM procedure, all samples were digested in acid to analyze the individual components. For NMR analysis approximately 5 mg of modified MOF was added to an NMR tube followed by 0.8 mL DMSO and 3 drops of DCl. NMR tubes were vortexed briefly and sonicated for 1 minute, whereby the solution took on a fluorescent green hue. The material was allowed to settle for 10 minutes and $^1$H NMR spectra was acquired. To quantify PSM, a small portion of the modified fiber was added to a vial with 0.8 mL dimethylsulfoxide (DMSO) and 3 drops of DCl. The solution was vortexed or shaken until the cotton returned to its original white color and the solution was transferred to an NMR tube for analysis of the ligand component. For mass spectrometry (MS) data approximately 1 mg of each modified sample was added to a 2 mL Agilent vial followed by 1 mL of MeOH and 1 drop of HCl. The vials were shaken by hand until all particulate was fully dissolved (approximately 5 minutes) and mass spectra was acquired using an Agilent 6224 Accurate Mass TOF LC/MS with electrospray and multi-mode (ESI/APCI) sources in negative or positive ion mode by direct injection in methanol. For each sample $[M-H]^-$ or $[M+H]^+$ was detected for both the unmodified and modified ligands. Thermal stability was evaluated using thermal gravimetric analysis (TGA) acquired with a TGA Q500 V20.13 Build 39 instrument with a ramp rate of 20° C./min under an inert flow of nitrogen from 25° C. to 800° C., and analyzed with TA Universal Analysis. Sample mass was approximately 1-5 mg. Powder X-Ray diffraction (PXRD) patterns were obtained using a Bruker D8 Discover DaVinci Powder X-ray Diffractometer with CuKα radiation operated at 40 kV and 40 mA. A 0.6 mm divergent slit was placed on the primary beam side and a high-resolution energy-dispersive LYNXEYE-XE-T detector on the diffracted beam side during the XRD studies. The instrument alignment was tested using the NIST 1976b SRM. A typical scan rate was 0.1 sec/step with a step size of 0.02 deg. Infrared (IR) data was acquired on a Nicolet 6700 FTIR spectrometer with all samples prepared as pressed potassium bromide (KBr) pellets. In short, approximately 5-10 mg of gently ground MOF was added to a clean 10 mL beaker followed by approximately 200 mg of FTIR grade potassium bromide. After thoroughly mixing samples were pressed to obtain sample containing KBr pellets. For copper MOF-cottons fibers, infrared (IR) data were acquired on a Nicolet 6700 Fourier transform infrared (FTIR) spectrometer under a nitrogen flow. Diffuse reflectance UV-Vis spectroscopy was performed using a Nicolet Evolution 300 UV-Vis Spectrophotometer equipped with a Praying Mantis diffuse reflectance accessory. To access MOF coverage of the cotton fibers, scanning electron microscopy (SEM) imaging was performed using a JEOL JSM-6500F microscope. An accelerating voltage of 5.0 kV and a working distance of 10.0 mm were used. All samples were placed under vacuum and coated with 20 nm gold prior to imaging. Five to six representative images were taken at three different magnifications for each sample. Cross-sectional transmission electron microscopy (TEM) imaging was performed to analyze the MOF crystals around individual cotton fibers using a JEOL JEM2100F microscope. For cross-sectioned TEM imaging samples were first embedded. In brief, samples were heated under vacuum at 22 psi and 70° C. for 30 min, embedded in a mixture of 70% resin, 30% acetone for 40 min on the rotator, followed by 100% resin for 1 h on the rotator, and finally transferred to flat embedding molds and heated under vacuum at 22 psi and 70° C. for 20 h. Sections were then cut on Reichert Ultracut E at 70 nm thick, and imaged. Additional TEM imaging was performed by isolating 1 cotton fiber. The fiber was drop casted using ethanol between 2 copper grids prior to imaging. This imaging includes bright field transmission electron microscopy (BFTEM), high angle annular dark field scanning transmission electron microscopy (HAADF-STEM), and high resolution TEM (HRTEM).

Example 1: Synthesis of 2-aminobenzene-1,3,5-tricarboxylic Acid

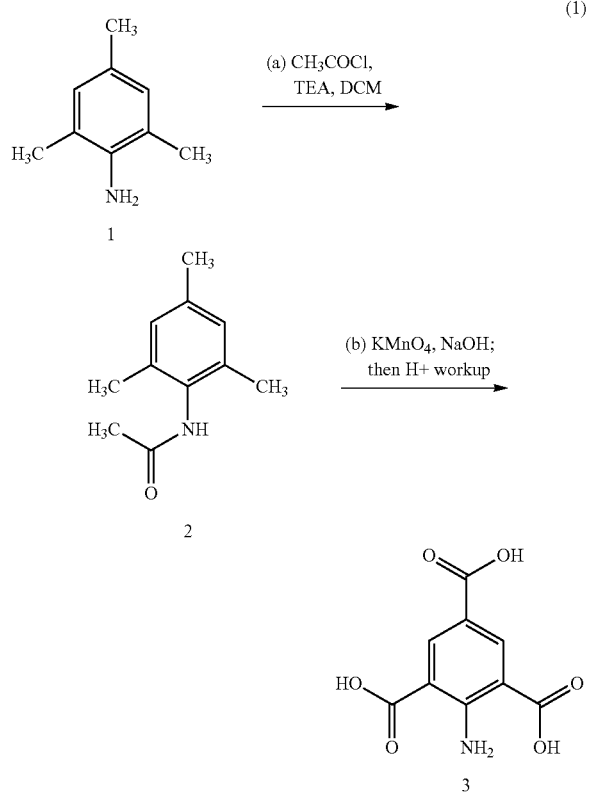

N-mesitylacetamide (2) was synthesized in two steps according to Formula 1 beginning with 2,4,6-trimethylaniline (1) via modifications to a known literature procedure (see Cai, Y., et al., Control of Metal-Organic Framework Crystal Topology by Ligand Functionalization: Functionalized HKUST-1 Derivatives. Crystal growth & design 2014, 14, 6122-6128). Under Argon atmosphere 2,4,6-trimethylaniline (10.5 mL, 75 mmol, 1 equiv) was added to a flame dried 500 mL round bottom flask equipped with a Teflon stir bar. 100 mL of dichloromethane was added while stirring and the flask was cooled to 0° C. Acetyl chloride (5.64 mL, 79 mmol, 1.05 equiv) was added dropwise via addition funnel, followed by triethylamine (11.01 mL, 79 mmol, 1.05 equiv). The reaction was monitored by TLC. When little to no starting material remained (approximately 2 hours), the reaction mixture was filtered. The solid was suspended in water for 30 minutes, collected by filtration, and dried overnight in vacuo to yield 9.5 grams, 72% N-mesitylacetamide (compound (2) of Formula (1)). Crude material was carried on without further purification. $^1$H NMR: (CDCl$_3$, 400 MHz, δ): 6.93, s, 2H; 2.29, s, 3H; 2.25, s, 6H; 1.73, s, 3H. $^{13}$C NMR: (CDCl$_3$, 101 MHz, δ): 169.0, 137.1, 136.3, 135.3, 129.2, 128.9, 23.18, 20.90, 19.75, 18.33. MS ESI-APCI found M+1=178.12. IR: (KBr pellet) ν (cm$^{-1}$)=3147, 3097, 2914, 2852, 2764, 2534, 2447, 1896, 1716, 1676, 1483, 1414, 1225, 766.

2-aminobenzene-1,3,5-tricarboxylic acid (compound (3) of Formula (1)) was synthesized from the crude N-mesitylacetamide, in a one-pot oxidation of the methyl substituents according to known methods (see Parola, S. et al., Optical Properties of Hybrid Organic-Inorganic Materials and their Applications. Adv. Funct. Mater. 2016, 26, 6506) and removal of the acetyl group. N-mesitylacetamide (5.0 g, 28.2 mmol, 1 equiv) was added to a 500 mL round bottom flask equipped with a Teflon stir bar and condenser followed by 165 mL deionized H$_2$O. NaOH was added (0.55 g, 14 mmol, 0.5 equiv) slowly in approximately 0.1 g portions over 5 minutes. KMnO$_4$ was added last (34 g, 215 mmol, 7.8 equiv) in approximately 5 g portions over 2 hours at room temperature. Once the KMnO$_4$ addition was complete, the reaction was stirred for 1 hour at room temperature and then heated to reflux at 85° C. for 72 hours. The resultant brown slurry was filtered through filter paper to remove MnO$_2$, and rinsed with 200 mL hot water. The clear filtrate was acidified with 20 mL concentrated HCl while stirring to a pH of 1-2. The mixture was refluxed overnight at 100° C. Upon cooling to room temperature the product crystallized in solution as a white solid. The solid was filtered and rinsed with 200 mL ice cold water yielding 3 grams, 40% of the product. $^1$H NMR: (DMSO-d6, 400 MHz, δ): 13.27 (s, 3H); 8.56 (s, 2H); 8.55 (s, 2H). $^{13}$C NMR: (DMSO-d6, 101 MHz, δ): 169.1, 166.6, 155.6, 138.7, 115.1, 112.0. MS ESI-APCI found M+1=226.03. IR (KBr pellet) ν (cm$^{-1}$) 3418, 3291, 3074, 1716, 1678, 1446, 1570, 1292, 1252, 1114, 1084, 883, 813, 694.

Example 2: Synthesis of MOF Cu$_3$(NH$_2$BTC)$_2$

The MOF was synthesized following modification to a known literature procedure (see Horcajada, P. et al., Metal-Organic Frameworks as Efficient Materials for Drug Delivery. Angew. Chem. Int. Ed., 2006, 45, 5974). In brief, 2-aminobenzene-1,3,5-tricarboxylic acid (510 mg, 2.65 mmol, 1 equiv) was added to a 100 mL Pyrex glass container followed by Cu(NO$_3$)$_2$.3H$_2$O (1.03 g, 4.26 mmol, 1.61 equiv). 5 mL H$_2$O and 40 mL DMA were added by syringe and the solution was mixed via sonication for 10 minutes.

The homogeneous solution was then heated to 85° C. for 42 hours and slowly cooled to room temperature. The resulting green/teal crystalline MOF material was collected by filtration and dried in air overnight. The MOF was then loaded into a cellulose thimble and was treated by Soxhlet extraction with ethanol for 20 hours to exchange the solvent. Lastly, the MOF was thermally activated in a vacuum oven at 120° C. for 20 hours yielding a dark green powder.

Example 3: Post-Synthetic Modification (PSM) of MOF $Cu_3(NH_2BTC)_2$

For each sample, $Cu_3(NH_2BTC)_2$ (75 mg, 0.2 mmol relative to the amine) was added to a 2-dram vial followed by 4 mL of $CHCl_3$ and soaked overnight. After 12 hours each vial was dosed with 1, 10, 20 or 40 equivalents of the desired anhydride. The heterogeneous mixtures were mixed via vortex for 3 seconds at 3000 RPM. Vials were then heated to 45° C. for 24 hours in a heating block. Upon cooling, the vials were centrifuged at 3000 RPM for 10 minutes. Solvent was decanted with a pipette and 4 mL clean $CHCl_3$ was added. The vials were vortexed once again, centrifuged, and the solution decanted. This was repeated 2 times. Once more $CHCl_3$ was added and soaked overnight. After 12 hours the vials were centrifuged and solvent decanted. The MOFs were dried in open atmosphere for 12 hours followed by 12 hours in the oven at 100° C. To remove residual chloroform, the material can be rinsed with methanol as described above; however, rinsing with methanol bears no impact on the hydrophobic effects observed, nor does it remove any additional byproduct observed.

Table 1 reports the percent conversion of $Cu_3(NH_2BTC)_2$ with anhydrides.

TABLE 1

| | | % Conversion | | | |
|---|---|---|---|---|---|
| Entry | MOF | 1 equiv | 10 equiv | 20 equiv | 40 equiv |
| 1 | $Cu_3(NH-AMiPr-BTC)_2$ | 6 ± 1 | 10 ± 6 | 11 ± 2 | 20 ± 6 |
| 2 | $Cu_3(NH-AMiBu-BTC)_2$ | 11 ± 0 | 28 ± 1 | 37 ± 0 | 43 ± 0 |
| 3 | $Cu_3(NH-AM4-BTC)_2$ | 14 ± 1 | 31 ± 1 | 43 ± 0 | 50 ± 3 |
| 4 | $Cu_3(NH-AM5-BTC)_2$ | 7 ± 4 | 20 ± 6 | 25 ± 8 | 32 ± 3 |
| 5 | $Cu_3(NH-AM6-BTC)_2$ | 13 ± 2 | 20 ± 5 | 27 ± 7 | 32 ± 1 |
| 6 | $Cu_3(NH-AM7-BTC)_2$ | 9 ± 1 | 18 ± 2 | 22 ± 2 | 26 ± 4 |
| 7 | $Cu_3(NH-AM10-BTC)_2$ | 6 ± 1 | 10 ± 1 | 11 ± 1 | 13 ± 1 |

FIG. 1 is a schematic illustration of PSM of an exemplary MOF with various anhydrides. All PSMs were performed three times using three independent $Cu_3(NH_2BTC)_2$ samples. Various batches of the MOF were used for each modification to confirm that the percent conversions were independent of the different batches of MOF used. The percent conversions were calculated by comparing the ratio of the aromatic chemical shifts associated with the unmodified and modified ligands in the $^1H$ NMR spectra of each independent acid digested material.

The data reported in Table 1 represents the average of the three modified samples and the standard deviation associated with those averages. The data of Table 1 demonstrates the reproducible control of a range of percent conversions for each different anhydride used. As the carbon chain of the PSM amide increases in length for linear aliphatic chains, a decrease in the maximum percent conversion is observed. In our study with $NH_2BTC$, chains as low as 4 carbons in length result in limited maximum conversions of 50%. Modifications with branched chain functionalities do not seem to fit this trend. We hypothesize that these observations may be due to steric hindrance, preventing access and diffusion of the anhydrides used for these reactions to the intended modification sites.

Complete conversion of $Cu_3(NH_2BTC)_2$ with anhydrides containing carbon lengths of 4 or more does not appear to be possible; however, this provides a unique opportunity to control mixed-ligand ratios within this framework and may be attributable to the decrease in disorder of the BTC system due to the increased substitution of the ligand. This is not often the case with mixed-ligand syntheses, wherein the ratio of mixed-ligands added to form the desired MOF does not predictably impact the percent incorporation of each ligand present in the resultant MOF formulation. The ability to reliably access mixed-ligand frameworks yields materials that have multiple distinctive pore environments that exhibit different chemical properties all within the same material. This type of control could permit multi-selective gas adsorption (among other multifunctional applications), due to the ability to tune a percentage of the ligands, and by default affect the properties of a desired percentage of pore sites within the same material.

Conversion limitations may also be advantageous for the retention of MOF crystallinity. Using acetic anhydride (2 carbons in amide), up to 92% conversion can be achieved, however, after 73% conversion substantial loss of crystallinity is observed. In this study, when using butyric anhydride with a 4 carbon chain, the maximum conversion is limited to 50% and the same degradation concerns are not observed. A close examination of the $^1H$ NMR spectra obtained from the digested modified MOFs shows that minor peaks are present, consistent with carboxylic acid byproduct generated during the formation of the amide. The presence of this byproduct may suggest that it is simply trapped within the MOF. Alternatively, the byproduct may be coordinating to the copper metal ions, replacing the labile ethanol ligands. This provides insight to a plausible mechanism for modification-related degradation. Nevertheless, even at maximum levels of modification, thermal gravimetric analysis indicates that the modified materials in this study maintain thermal stability as compared with the unmodified material.

Figure 2:
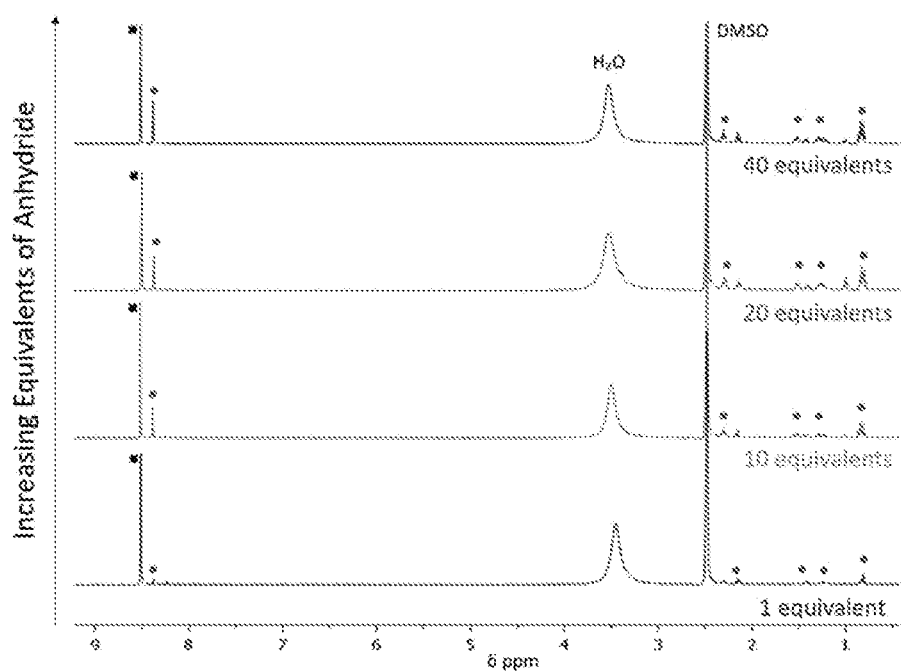
FIG. 2 is $^1$H NMR spectra after acid digestion with DCl in DMSO-d6 of modified $Cu_3(NH_2BTC)_2$ with valeric anhydride.

Little to no effect on conversion was achieved when increasing equivalents beyond 40, increasing reaction time, or with increasing temperature of the reaction. FIG. 2 is $^1H$ NMR spectra after acid digestion with DCl in DMSO-d6 of modified $Cu_3(NH_2BTC)_2$ with valeric anhydride to confirm synthesis of $Cu_3(NH-AMS-BTC)_2$. All samples were dried at 100° C. for 12 h and digested in 0.8 mL DMSO with 2 drops of DCl.

In FIG. 2, the mass [M–H]– of both the unmodified and modified linkers were abundant in the digested mass spectrum of each modification, which confirmed mixed-ligand functionalization. The appearance and intensity of a chemical shift within the $^1H$ NMR spectra of the digested MOF samples at 8.39 ppm, indicative of the aromatic protons on the modified amino tricarboxylate ligands was identified. The unmodified ligand peaks are denoted with a black square and appear slightly downfield of the modified ligands denoted with red circles. The two peaks in the aromatic region (8 ppm-9 ppm) were used to quantify the conversion ratio of modified to unmodified ligands after PSM. FIG. 2 illustrates that as the equivalents of anhydride increases, so does the percentage of modification, denoted by the peak in the aromatic region with the red circle.

Example 4: Wettability Studies

Contact Angle Goniometry (CAG) was performed to analyze the interaction of the materials with water using a Krüss DSA30 goniometer with ultrapure water. CAG was used to observe contact angles achieved after modification as to compare the sorptive rates of the materials at varying amounts of conversion.

Approximately 10 mg of each MOF powder was gently ground and added to a glass slide. Using another glass slide the material was carefully pressed to 2 mm in height. Videos were collected at 25 frames per second for 10 seconds. All water contact angles (WCA) were determined with a 6-8 μL droplet of water, whereby contact angles were calculated at 1 second after deposition. For less hydrophobic materials, measuring a static WCA was not possible. Therefore, water sorption rates were determined using 1 μL droplets of water. The time which the water droplet made contact with the material was subtracted from the time at which the entire water droplet went into the material. This value in milliseconds was used to determine the rate that 1 μL took to sorb into the material and is reported as the sorption rate in μL/s. The values given represent the average and standard deviation of three independent trials.

Water sorption rates were calculated using 1 μL droplets and the total time necessary to completely sorb 1 μL of water into the powder was used to determine a relative sorption rate for the resultant material after minimum and maximum conversions. As samples increased in hydrophobic character, water droplets of 1 μL would not deposit on the surface of the material; for these samples 6-8 μL water droplets were dispensed and contact angles were calculated 1 second after the droplet made contact with the MOF material.

Table 2 reports the sorption value and water contact angle for the modified MOF samples based on three averaged independent water droplet experiments.

TABLE 2

| Entry | MOF | % Conversion | Sorption (μL/s) | Contact Angle |
|---|---|---|---|---|
| 1 | $Cu_3(NH_2BTC)_2$ | 0 | 8.8 ± 0 | n/a |
|   |   | 6 ± 1 | 1.8 ± 0.1 | n/a |
| 2 | $Cu_3(NH\text{-}AMiPr\text{-}BTC)_2$ | 20 ± 6 | 1.5 ± 0.3 | n/a |
|   |   | 11 ± 0 | 4.1 ± 1.6 | n/a |
| 3 | $Cu_3(NH\text{-}AMiBu\text{-}BTC)_2$ | 43 ± 0 | n/a | 94.9 ± 1.3 |
|   |   | 14 ± 1 | 7.8 ± 1.9 | n/a |
| 4 | $Cu_3(NH\text{-}AM4\text{-}BTC)_2$ | 50 ± 3 | 1.02 ± 0.4 | n/a |
|   |   | 7 ± 4 | 0.46 ± 0.1 | n/a |
| 5 | $Cu_3(NH\text{-}AM5\text{-}BTC)_2$ | 32 ± 3 | n/a | 118.2 ± 0.9 |
|   |   | 13 ± 2 | 0.63 ± 0.2 | n/a |
| 6 | $Cu_3(NH\text{-}AM6\text{-}BTC)_2$ | 32 ± 1 | n/a | 126 ± 5 |
|   |   | 9 ± 1 | 1.21 ± 0.2 | n/a |
| 7 | $Cu_3(NH\text{-}AM7\text{-}BTC)_2$ | 26 ± 4 | n/a | 127 ± 6 |
|   |   | 6 ± 1 | n/a | 66 ± 6 |
| 8 | $Cu_3(NH\text{-}AM10\text{-}BTC)_2$ | 13 ± 1 | n/a | 147 ± 6 |

The water contact angle was performed by Contact Angle Goniometry (CAG). In the CAG experimentation the standard deviation shown is associated with the average of the three separate rates acquired for the sample. When contact angles could be determined, 6-8 μL droplets were used. The contact angles reported are the average of three independent droplet contact angles after 1 second of water deposition, and the standard deviations reported are the respective calculated standard deviations. Contact angles were plotted versus the number of carbons in the PSM amide modification. A linear fit was plotted with an equation of $y=5.7x+89.5$, $R^2=0.97$. Each data point represents the average of three trials. Error bars represent the standard deviation of 3 separate water droplets. By inserting a desired number of carbons in the carbon chain length for x, one can solve for the observed contact angle, y. Alternatively, if a desired contact angle is inserted for y, an estimated number of carbons needed in the amide chain can be deduced by solving for x.

The hydrophobicity of the material closely correlates to the modification and overall percent of modification. $Cu_3(NH_2BTC)_2$ exhibits a similar sorption rate as $Cu_3(BTC)_2$ at 8.8 μL/s. All of the modified material has slower sorption rates than the unmodified material, demonstrating that all of the modifications made increase the hydrophobic character of the MOF, albeit to different extents. For instance, $Cu_3(NH\text{-}AMiBu\text{-}BTC)_2$ with 11% conversion results in nearly half the sorption rate of the unmodified material, sorbing water at a rate of 4.1±1.6 μL/s. Additionally, nearly all materials exhibit greater hydrophobicity with slower sorption rates or contact angles achieved using 40 equiv of anhydride versus 1 equiv. Materials displaying contact angles from 90°-150° are considered hydrophobic. Maximum percent modifications with 5 or more carbons in the alkyl chain result in contact angles from 95°-147°, rendering these new mixed-ligand systems hydrophobic. Upon increasing modification to nearly 32% with valeric anhydride, sorption rates are significantly decreased so that after 1 s, a water contact angle of 118±4° is achieved. Unexpectedly, as little as 6% modification with decanoic anhydride led to a contact angle of 66±6°. At 13% conversion an impressive hydrophobic effect was achieved where the material exhibited an observed contact angle of 147±6°.

Figure 3:
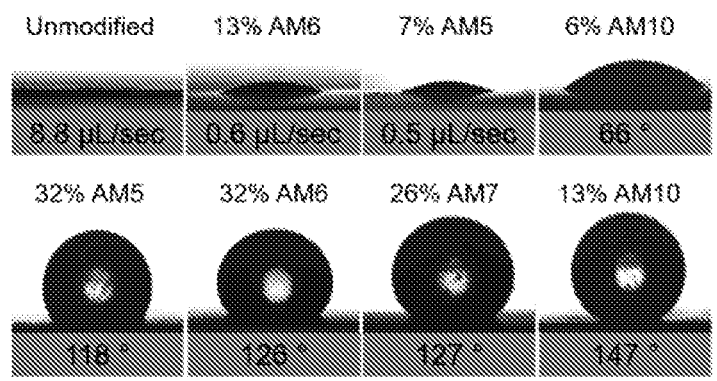
FIG. 3 is CAG images of water on the surface of a MOF.

Over the course of these experiments, several intriguing trends were identified. Increased hydrophobicity and slower sorption rates are achieved with straight-chain versus branched moieties. This holds true for both 4 and 5 carbon modifications; such as valeric versus isovaleric, and butyric versus isobutyric anhydrides. The modified samples displayed distinctive hydrophobic properties, whereby the MOF powder spread over the entire surface of the water droplet during CAG experiments. FIG. 3 are CAG images of water on the surface of a MOF. The images show tunable wettability with different modification. This may indicate a change in adhesion properties or electrostatic charge in the modified materials. These observations may be a consequence of changes in mechanical interlocking, inter-particulate forces of cohesion, liquid bridging or moisture-induced particle adhesion or reduced particle stiffness. These properties are not observed with the unmodified materials, further supporting the capability of late-stage functionalization to tune the chemical properties of the material. Superhydrophobic materials are characterized by contact angles >150°, accordingly this suggests that modifying $Cu_3(NH_2BTC)_2$ can yield near superhydrophobic powders. This data indicates modifications have a relatively significant impact on the hydrophobicity of this material, resulting in varied sorption rates.

Figure 4:
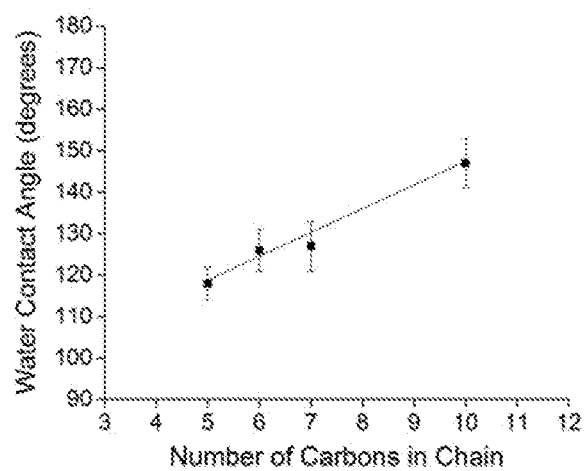
FIG. 4 is a plot illustrating that the water contact angle increases as the number of carbons in the linear chain increases.

FIG. 4 is a plot illustrating that the water contact angle increases as the number of carbons in the linear chain increases when the material is modified at maximum conversion. The values and standard deviation shown are the average of three independent experiments. The linear relationship allows for deliberate modification to access the desired level of hydrophobic character. This observation may suggest either the entire surface or a particular pore is modified on the MOF leading to predictable contact angles. Using the linear fit, one or two more carbons to the alkyl chain may produce superhydrophobic material with calculated contact angles approximately 152-158°.

Example 5: Structural Stability in Water Studies

As an example to test the stability of the MOF in water, approximately 10 mg of $Cu_3(NH_2BTC)_2$, or modified MOF was added to a 20 mL glass vial. Slowly, 5 mL of Millipore water was poured into each vial. Vials sat undisturbed for 30 minutes, after which Kimwipes were used to absorb the water. The material was dried for 1 hour in open atmosphere, followed by 1 hour in the oven at 100° C. and immediately analyzed with PXRD and Scanning electron microscope (SEM) imaging. SEM imaging was performed using a JEOL JSM-6500F microscope prior to and after water exposure. An accelerating voltage of 15.0 kV and a working distance of 10.0 mm were used. All samples were placed under vacuum and coated with 10 nm gold prior to imaging. Five to six representative images were taken at three different magnifications for each sample.

Figure 5:
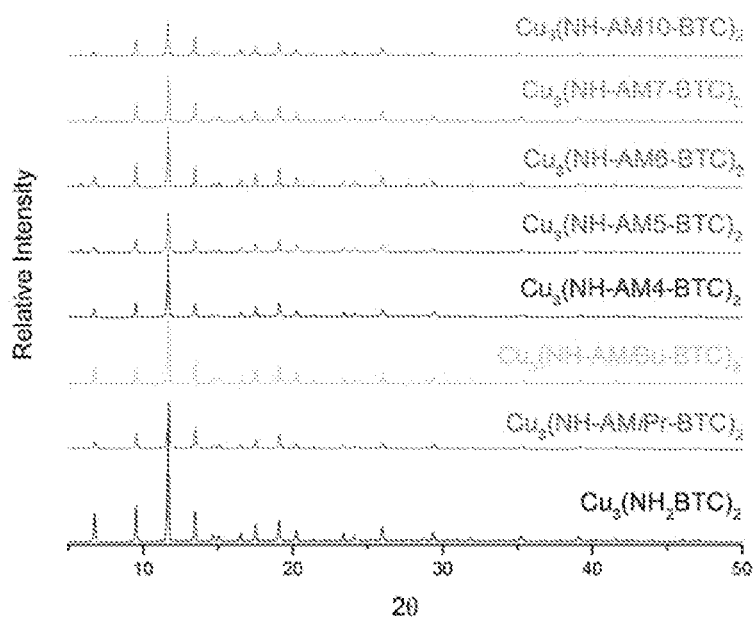
FIG. 5 provides powder x-ray diffraction patterns for samples modified with 40 equivalents of anhydride to amine.

FIG. 5 provides PXRD patterns for samples modified with 40 equivalents of anhydride to amine. The PXRD reveals crystallinity is retained after each modification with 40 equivalents of anhydride to amine as evidenced by patterns having matching 2θ reflections. This demonstrates that the disclosed covalent PSM approach with $Cu_3(NH_2BTC)_2$ allows reliable access to mixed-ligand frameworks having conversions ranging from 6-50% with a retention of structural integrity.

Figure 6:
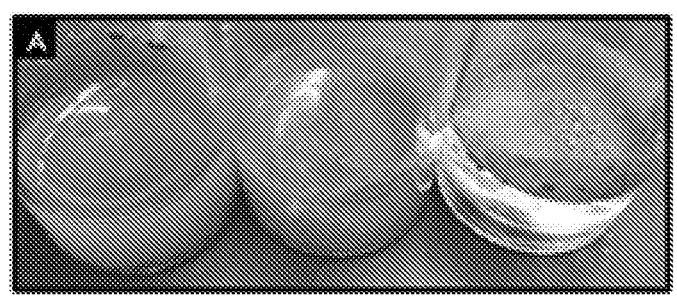
FIG. 6 is an image of a modified powder materials in vials containing water.
Figure 7:
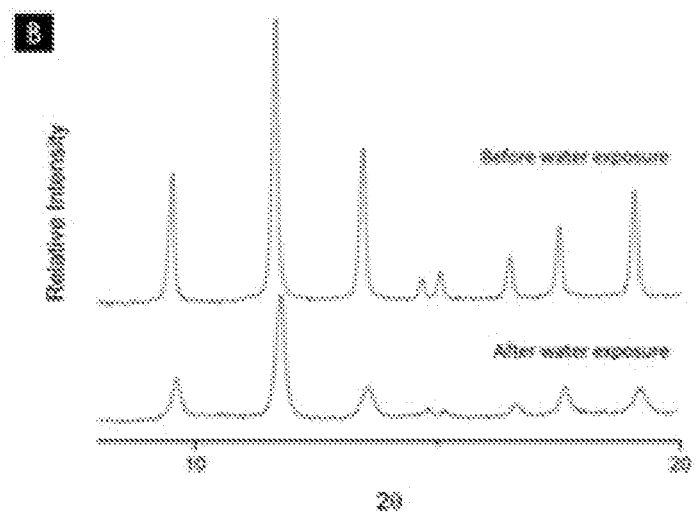
FIG. 7 provides powder x-ray diffraction of $Cu_3(NH-AM10-BTC)_2$ before and after 30 minutes of submersion in water.

Example 6: Enhanced Stability to Water $Cu_3(NH_2BTC)_2$ as well as $Cu_3(NH-AMiBu-BTC)_2$ and $Cu_3(NH-AM10-BTC)_2$ with maximum conversions were added to 3 separate 20 mL glass vials and 5 mL of water was added to each for 30 minutes. FIG. 6 is an image of the modified materials in the vials, in which the modified materials are from left to right $Cu_3(NH_2BTC)_2$, $Cu_3(NH-AMiBu-BTC)_2$ and $Cu_3(NH-AM10-BTC)_2$. As shown, the modified materials did not remain at the bottom of the vial, and were dispersed around and at the surface of the water, demonstrating enhanced hydrophobic character. This was especially apparent with $Cu_3(NH-AM10-BTC)_2$ (FIG. 6, far right). Upon removal of the water and adequate drying, the powder was analyzed. FIG. 7 is the PXRD pattern of $Cu_3(NH-AM10-BTC)_2$ before and after 30 minutes of submersion in water. FIG. 7 shows a crystalline material was present after water submersion. Conversely, $Cu_3(NH_2BTC)_2$ no longer exhibited well resolved peaks in the diffraction pattern after water submersion. These results demonstrate that modifying the MOF with 14% decanoic anhydride renders this material significantly more stable in aqueous environments.

Figure 8:
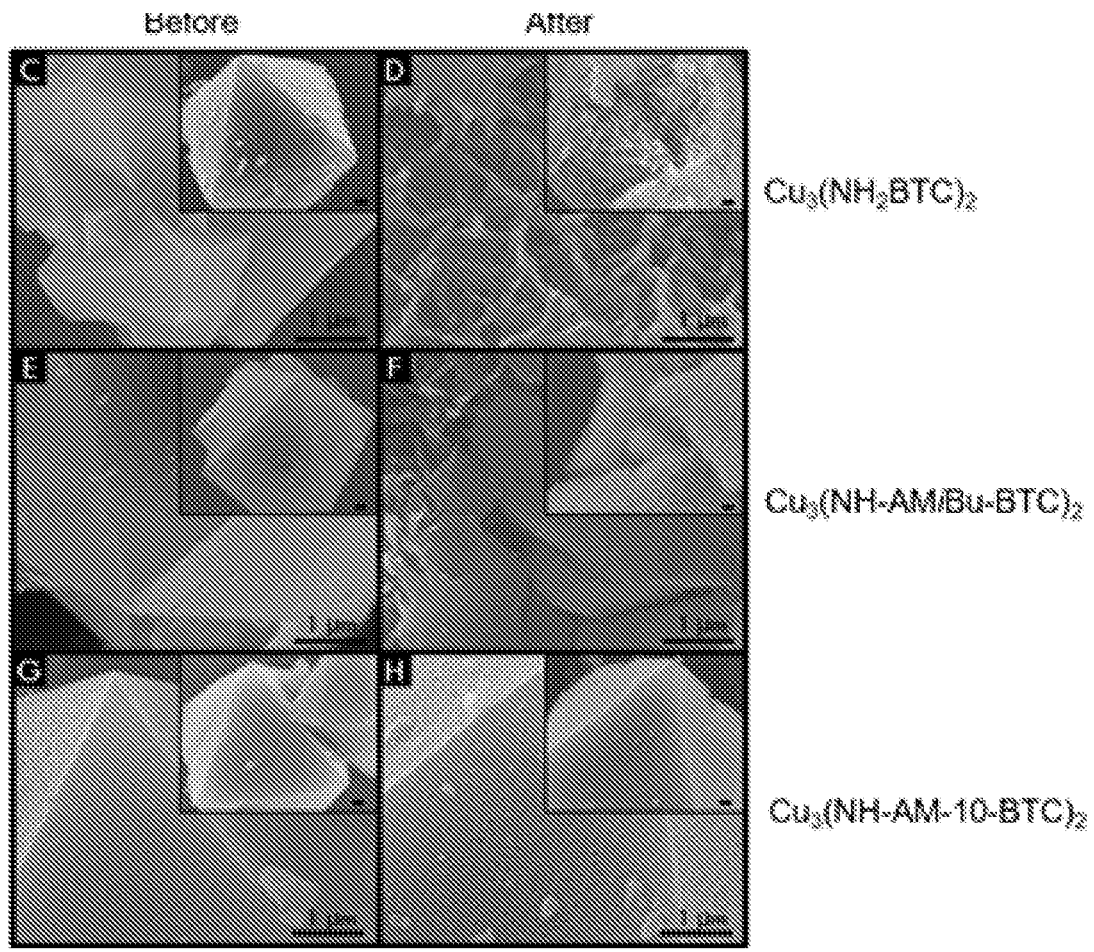
FIGS. 8C-8H are SEM images of samples before and after water submersion.

$Cu_3(BTC)_2$ is known to rapidly degrade in water-rich environments. FIGS. 8C-8H are SEM images of samples before and after water submersion. FIGS. 8C and 8D show that $Cu_3(NH_2BTC)_2$ is comparable to $Cu_3(BTC)_2$ with regard to surface deterioration upon water submersion. Prior to water submersion, the surface of $Cu_3(NH_2BTC)_2$ appears smooth and uniform. After submersion there is significant change to the morphology of the MOF; pores are expanded and the original octahedral crystals are nearly impossible to distinguish. $Cu_3(NH-AMiBu-BTC)_2$ still appears to undergo minor surface alteration exhibiting a more roughly textured morphology with breaks and cracks, albeit much less severe than in the unmodified material. $Cu_3(NH-AM10-BTC)_2$ on the other hand, showed little to no impact to the surface characteristics after being submerged in water.

Figure 9:
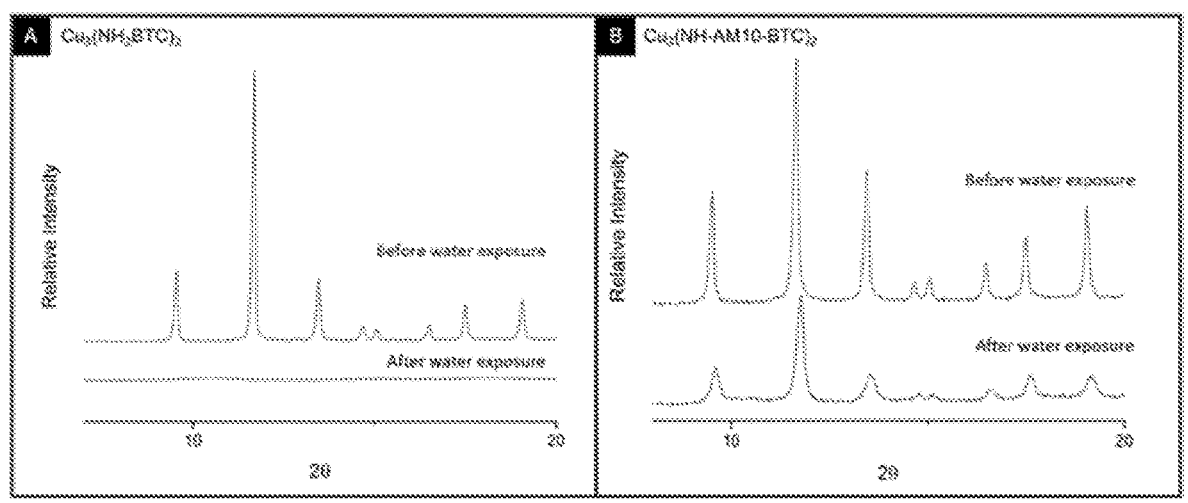
FIGS. 9A and 9B are PXRD patterns of $Cu_3(NH-AM10-BTC)_2$ and $Cu_3(NH_2BTC)_2$ on a sample material after water submersion FIG. 10 schematically illustrates an exemplary process to carboxymethylate and grow the MOF $Cu_3(NH_2BTC)$ using a layer-by-layer process on the surface of cotton fabric.

FIGS. 9A and 9B are PXRD patterns of $Cu_3(NH-AM10-BTC)_2$ and $Cu_3(NH_2BTC)_2$ on the material after water submersion. The PXRD patterns of FIGS. 9A and 9B verify that the modified material retained crystallinity after water submersion. The water submersion results indicate that tunable degradation rates are achievable by modifying $Cu_3$-(NH_2BTC)_2$. These results suggest the stability of the material correlates with the relative amount of hydrophobicity observed. This technique can be used with other modifications made herein to assess stability to water after modification. Taken together, this data showcases the elevated hydrophobic character of the modified material and its immunity to moisture damaging effects present with $Cu_3(BTC)_2$.

Example 7: Carboxymethylation of Cotton Swatch

Figure 10:
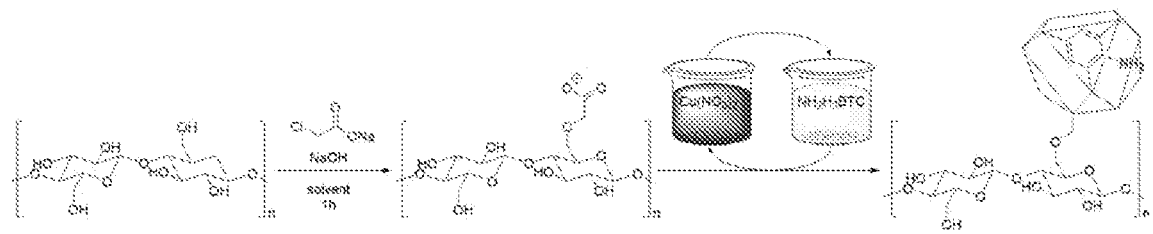

FIG. 10 schematically illustrates a process to carboxymethylate and grow the MOF $Cu_3(NH_2BTC)$ using a layer-by-layer process on the surface of cotton fabric. First, a 15 wt % NaOH (15 g per swatch) solution was prepared with 100 mL of 2:1 absolute ethanol/deionized water per swatch. Precut cotton swatches with dimensions 4.5 cm×2 cm were added and gently stirred for 30 min. The swatches were removed and sodium chloroacetate added to the original solution to attain a 1 M solution (11.6 g). After complete dissolution, the swatches were added back to the solution and gently stirred for 1 h. The resultant modified cotton was soaked for 30 min in Millipore water and rinsed with 100 mL Millipore water, followed by 100 mL ethanol. After drying in open atmosphere, the modified swatches were dried in an oven for 1 h at 60° C.

Example 8: Layer-by-Layer Growth Process of $Cu_3(NH_2BTC)_2$ on Modified Cotton Uniform growth of the MOF onto the cotton fibers of the carboxylated or modified cotton swatch was achieved via layer-by-layer dip coating process using a mechanical dip coater. Each swatch was dipped into independently prepared copper and ligand containing solutions. In a typical procedure, 20 mL scintillation vials were first filled with 20 mL of solution. Copper containing solution A was prepared using 1:1:1 dimethylacetamide (DMA), ethanol, Millipore water and 1.90 g copper (II) nitrate. The ligand, 2-aminobenzene-1,3,5-tricarboxylic acid, was synthesized following our previously reported procedure. The ligand containing solution B was prepared using 2:1:1 DMA, ethanol, Millipore water and 675 mg of the ligand. All solutions were vortexed, shaken, and sonicated (10 min) to ensure all compounds were completely dissolved. The solutions were transferred to 20 mL beakers. Carboxymethylated cotton swatches trimmed to 1.7 cm×3.8 cm were loaded to a mechanical dip coater and hydrated with absolute ethanol. The materials were then dipped into solution A for 17 min, a solution of ethanol for 5 sec, solution B for 17 min, followed by ethanol for 5 sec. The process was repeated for a total of 15 cycles (30 total layers, 15 of each solution A and B). To remove any residual nonbonded copper or ligand, swatches were soaked in 20 mL of ethanol overnight. After this time, each swatch was added to a new solution of ethanol, washed and vortexed six times with new solvent in a new vial each time.

Figure 11:
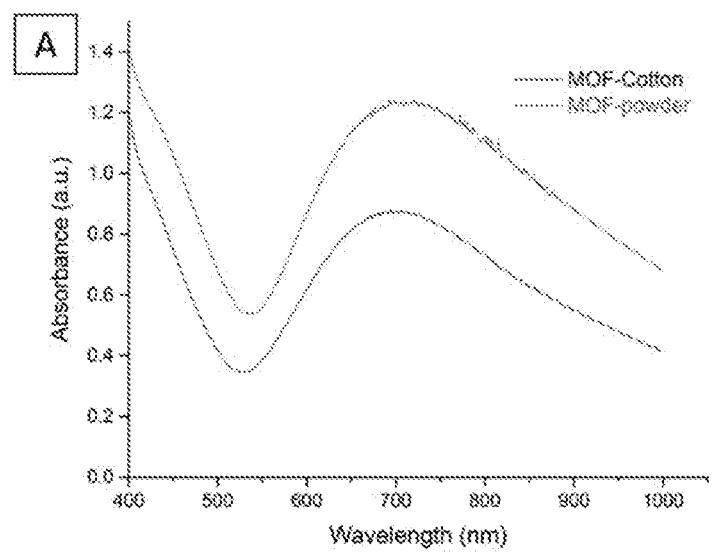
FIG. 11 is a diffuse reflectance UV-Vis of samples.

Diffuse reflectance UV-Vis and PXRD were performed to confirm the presence and orientation of the crystalline MOF on the surface of carboxymethylated cotton. FIG. 11 is a diffuse reflectance UV-Vis of the MOF-powder (top) and MOF-cotton (bottom) materials, showing the presence of the MOF on cotton. A characteristic absorbance peak around 700 nm is observed, indicating the MOF grown on cotton exhibits nearly the same diffuse reflectance of dispersed light inside the crystalline lattice as the MOF powder. This suggests the MOF is indeed present on the surface of the carboxymethylated cotton, and would be expected to behave electronically like the MOF powder itself.

Figure 12:
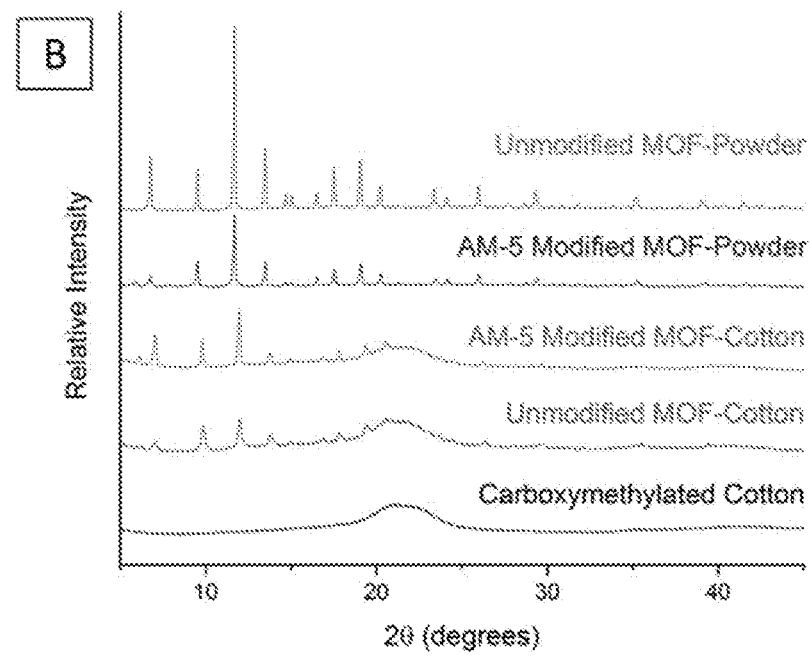
FIG. 12 is PXRD data of samples.

FIG. 12 is PXRD data indicating the crystalline MOF on the surface of carboxymethylated cotton. Furthermore, the diffractogram of the unmodified MOF-cotton composite supports that the crystallinity of the carboxymethylated cotton is retained and the MOF particles on cotton have the same morphology and orientation as the MOF powder materials. This is evidenced by sharp Bragg reflections at relevant 2θ with matching relative peak intensities.

Figure 13:
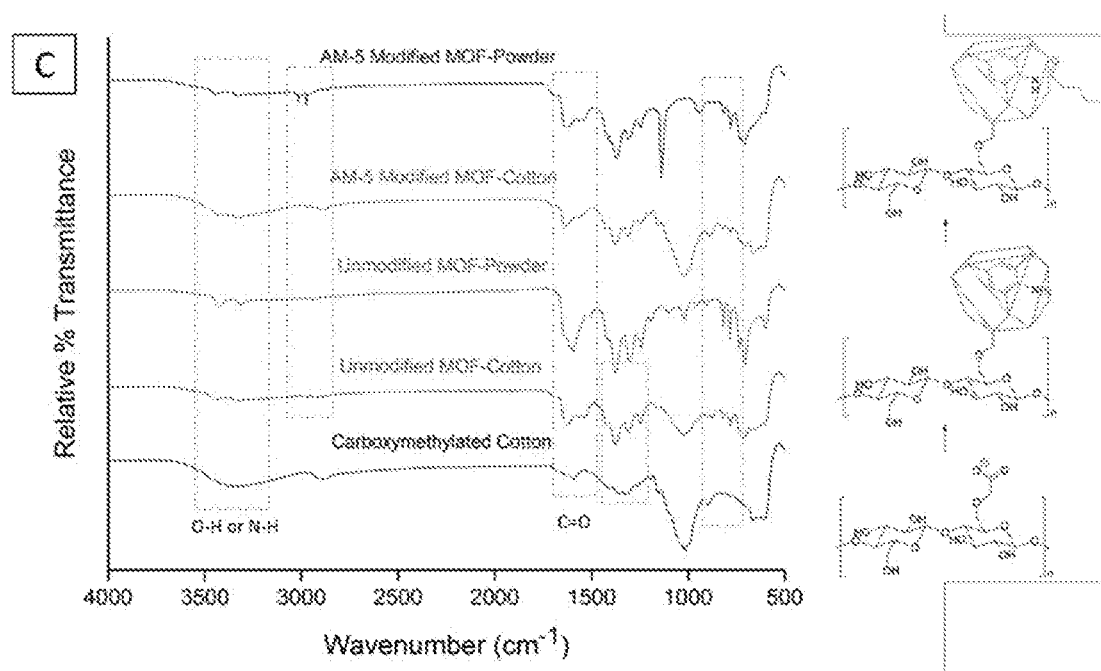
FIG. 13 is IR spectroscopy of MOF-powder and MOF-cotton samples.

FIG. 13 is IR spectroscopy of the MOF-powder and MOF-cotton samples. The IR spectroscopy shows a clear difference between the carboxymethylated cotton and the MOF grown on cotton. The unmodified MOF cotton contains several characteristic features of the MOF, as observed by comparison with the MOF powder. With MOF present, distinct features at 3400 $cm^{-1}$ shows the presence of an amine, a new feature at 1640 $cm^{-1}$ is representative of the C=O stretch associated with the MOF, and features within the thumbprint region between 750 $cm^{-1}$ and 850 $cm^{-1}$ are also present. Taken together this data indicates that the cotton contains crystalline MOF crystals uniformly on the surface.

Figure 14:
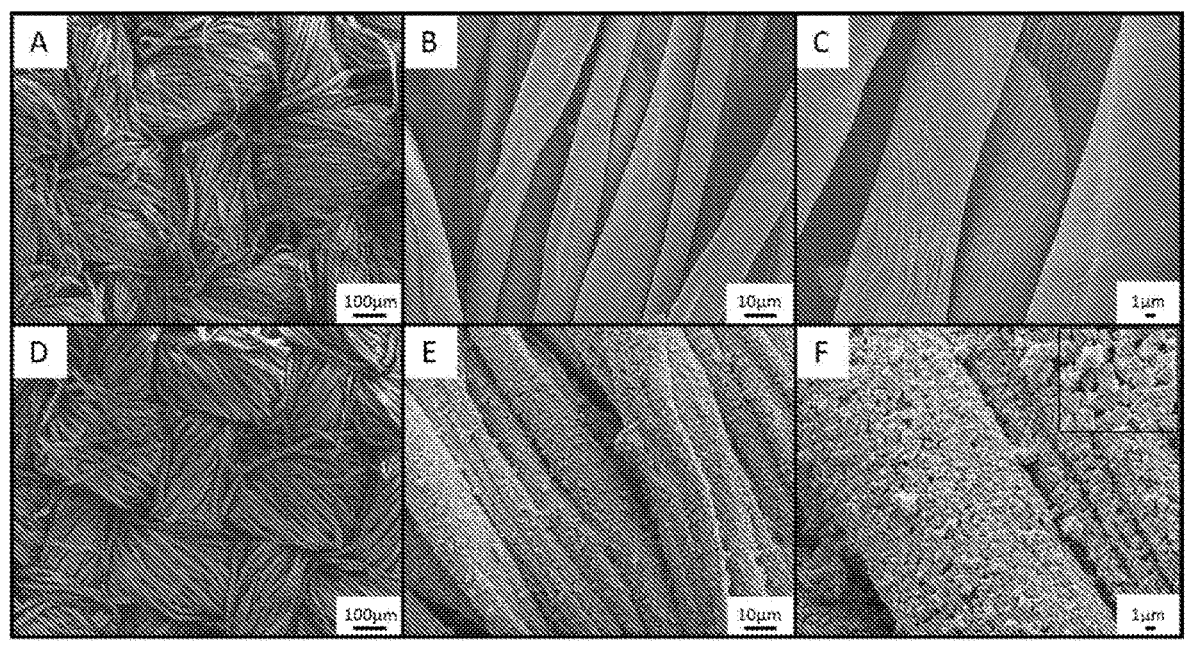
FIG. 14 are SEM images taken at 5 kV of exemplary MOF-cotton materials.

Surface coverage of the MOF onto cotton fibers was investigated and analyzed using SEM and TEM imaging. Coverage of cotton surface was adjusted by varying the number of layers made and deposition time allowed. Complete and consistent coverage of the cotton fibers was accomplished with 17 min in each solution and with at least 30 total layers (15 times in each copper or ligand solution). As previously mentioned, the use of a mechanical dip coater ensured uniformity between individual MOF-cotton swatches. FIG. 14 are SEM images taken at 5 kV of the MOF-cotton materials showing excellent surface coverage of the MOF fibers. FIGS. 14A-14C are images of natural cotton. Images 14D-14F are image of the MOF immobilized onto the cotton fibers. As shown, The MOF crystals individually appear to be approximately 1 μm in diameter with little twinning of the crystallites. The SEM imaging reveals that the resultant materials contain consistent full coverage of the surface of the cotton swatches with abutting MOF crystals of uniform size and morphology.

Figure 15:
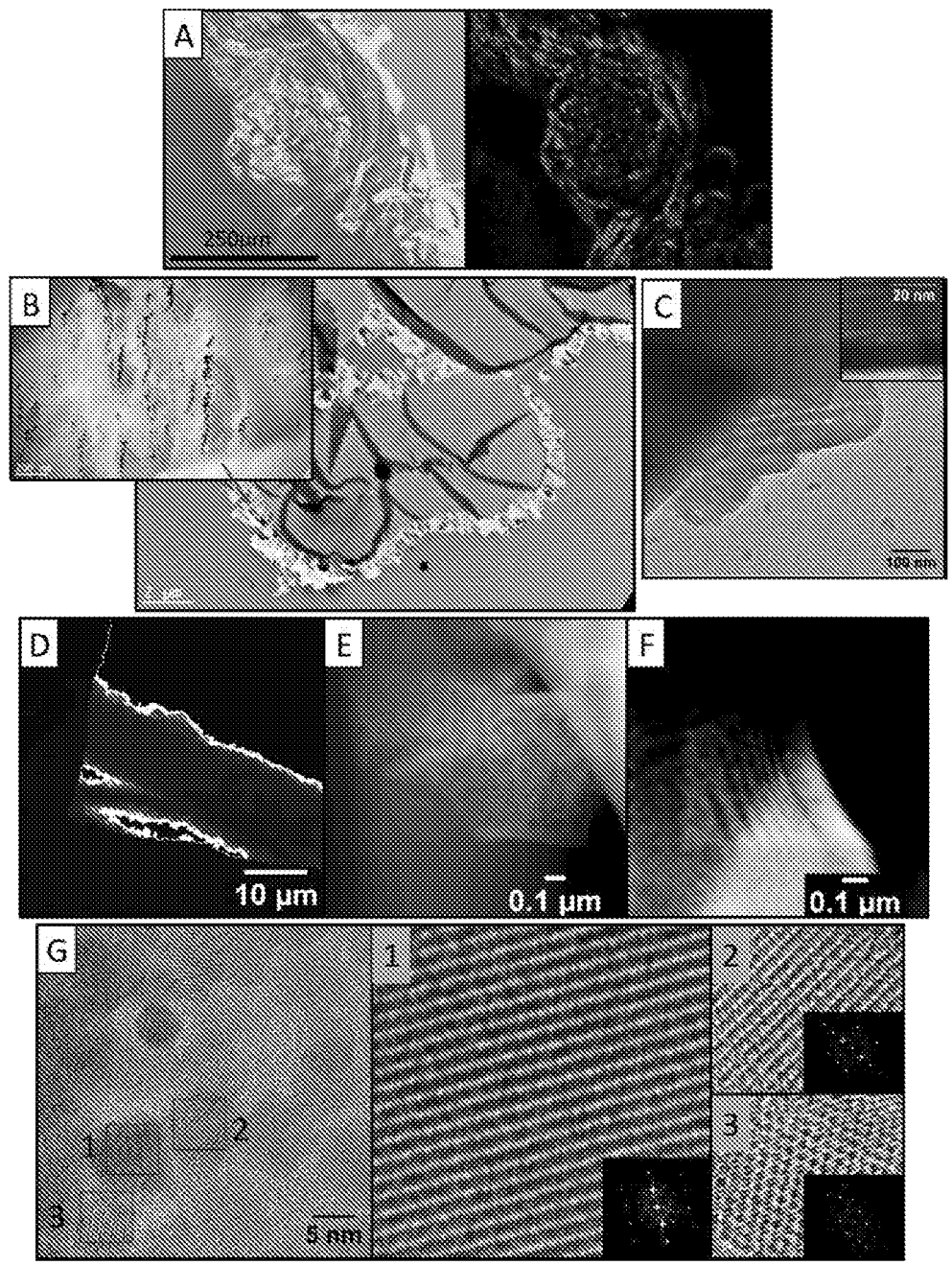
FIG. 15A is an SEM image of a cross-sectioned exemplary MOF-cotton material and EDS mapping of copper.
FIG. 15B are TEM images of a cross-sectioned exemplary MOF-cotton material.
FIG. 15C is an BFTEM image of a MOF crystal anchored on cotton material.
FIG. 15D-15F are HAAD-STEM images of MOF crystals.
FIG. 15G are HRTEM images of the MOF crystals.

To analyze MOF coverage around the entire cotton fiber, the material was cross-sectioned and analyzed with SEM and TEM imaging. FIG. 15A is an SEM image of the cross-sectioned MOF-cotton material and EDS mapping of copper. The SEM imaging coupled with EDS mapping of a cross section of the MOF-cotton material shows copper is present around the entire surface of the individual cotton fibers.

FIG. 15B are TEM images of embedded and cross-sectioned MOF-cotton material showing coverage around the entire cotton fiber. The TEM imaging of the cross sectioned material reveals that the optimized conditions generate a single uniform layer of adjoining crystallites around each cotton fiber roughly 1 μm×1 μm in size. This indicates the detailed growth parameters maximize the surface area and size of each individual MOF crystal attached, as opposed to increasing the number of MOF crystals on the surface.

FIG. 15C is an BFTEM image of a MOF crystal anchored on cotton material. As shown in the image, the individual MOF crystals displayed distinct ligand and copper layers as light and dark layered regions of the BFTEM images FIG. 15D is a HAAD-STEM image of MOF crystals on the surface of a single fiber of MOF-cotton material. In FIG. 15D, the surface of the fiber appears entirely covered with MOF crystals. Higher magnification further supports this conclusion. FIG. 15E is a HAAD-STEM image of 2 MOF crystals on MOF-cotton material. FIG. 15F is a HAAD-STEM image of one MOF crystal on MOF-cotton material, in which lines of copper are visible.

To further assess the crystallinity and orientation of the crystals, free particles liberated during isolation of a single MOF-cotton fiber were imaged using HRTEM. FIG. 15G are HRTEM images. Magnification of the framed regions are shown with insets of the associated Fourier transforms. Several crystal orientations are shown depicting regularly arranged channels throughout the crystals. Taken together, the imaging data suggests that the detailed methodology is advantageous for ensuring that natural cotton is sufficiently carboxymethylated to yield increased crystalline MOF growth around the entire surface of individual modified cotton fibers. Additionally, this method results in the uniform growth of MOF $Cu_3(NH_2BTC)_2$ octahedral crystals on the surface of each individual cotton fiber.

Example 10: Postsynthetic Modification of $Cu_3(NH_2BTC)_2$ on Modified Cotton

After the MOF-cotton composites were characterized, the swatches were subjected to PSM with valeric anhydride. The swatches were submerged in a 1.5 M solution of valeric anhydride in $CHCl_3$ for 24 h. The MOF-cotton composites were added to 20 mL scintillation vials followed by 12 mL $CHCl_3$ and 3.55 mL valeric anhydride and vortexed to mix. After 24 h of soaking, the cotton swatch was removed, rinsed several times with $CHCl_3$ and soaked overnight. Each swatch was subsequently soaked in ethanol for 24 h, after which time the solution was decanted, swatches rinsed with 100 mL ethanol, and then swatches dried in the oven at 60° C. for 1 h.

Example 11: Copper Releasing Studies

Soaking studies were performed to test the rate at which the materials released copper into aqueous environments under biologically relevant conditions. MOF-cotton composites were first cut to 0.7 cm×0.7 cm individual pieces and placed into 4 dram vials. 1 mL of NBM solution was added and the materials were incubated at 37° C. for various time points. After the intended time, the solutions were pipetted into a new vial, diluted with 4 mL Millipore water and analyzed by inductively coupled plasma optical emission spectrometry (ICP-OES) detection. Each data point reported is representative of 3 trials from 3 independent swatches with the standard deviation.

The rate of copper release from the materials was carefully monitored over various time points and are reported in Table 3.

TABLE 3

| Time (h) | MOF-Cotton (μmol · $cm^{-2}$) | AM-5 Modified Cotton (μmol · $cm^{-2}$) |
|---|---|---|
| 0.5 | 3.21 ± 0.21 | 2.55 ± 0.08 |
| 1 | 3.70 ± 0.42 | 3.07 ± 0.10 |
| 2.5 | 4.10 ± 0.11 | 3.85 ± 0.20 |
| 6 | 5.28 ± 0.36 | 5.16 ± 0.22 |
| 12 | 5.01 ± 0.11 | 5.76 ± 0.17 |
| 24 | 5.18 ± 0.07 | 6.15 ± 0.10 |

The modified materials were found to release less copper into solution within the first 6 h than the unmodified materials. The unmodified MOF-cotton initially releases $Cu^{2+}$ ions into solution most quickly over the first 6 hours, after which time copper release remains slow and consistent. If the material is post-synthetically modified, initially slower release of $Cu^{2+}$ ions is observed than the unmodified material. After 6 h, the modified material releases $Cu^{2+}$ ions at a faster rate than the unmodified material. Modification of the MOF yields interesting changes to the releasing capabilities of the material. Both modified and unmodified materials continue to slowly release $Cu^{2+}$ ions beyond the 24 h tested. At 24 h, the modified material has released ~90% of the total copper content, while the unmodified material has released just ~54% of the total copper content. These results suggest that these materials may be advantageous for slow and controlled release of Cu2+ ions.

Figure 16:
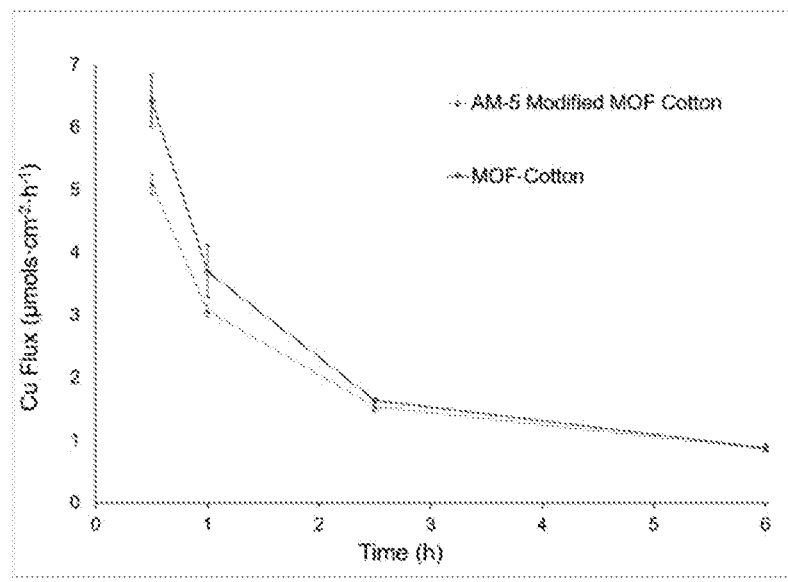
FIG. 16 is a plot of the copper flux of samples for the first 6 hours of exposure.

FIG. 16 is a plot of the copper flux of each sample for the first 6 h. The rate of copper flux of the unmodified material at 30 min is significantly greater than the modified MOF. At 1 h, the MOF-cotton material still exhibits a greater flux than the unmodified material. After 2.5 h, the materials begin to behave similarly and slowly release $Cu^{2+}$ ions. After 6 h, copper ions are continually released for both materials at a flux less than or equal to 0.9 $\mu mols \cdot cm^{-2} \cdot h^{-1}$. Based on previous reports of PSM yielding more stable materials, we anticipated the modified material would release copper ions slower than the unmodified. Conversely, the results of PSM to the materials leads to an increase in the copper flux. While the results with valeric anhydride are not what was hypothesized, they excitingly suggest that this strategy does indeed yield tunable materials. As such, these findings serve as necessary precedence to encourage further exploration using PSM of MOFs in textile materials for controllable ion release.

FIG. 13 is PXRD of the MOF-cotton materials after 1 h of being submerged in NBM at room temperature. The results reveal that while these materials are releasing copper, the MOF retains crystallinity. These results are particularly interesting when compared to previous reports investigating the biocompatibility of MOF coatings on solid Au surfaces and the stability to water and complex media of the materials. Notably, similar copper-SURMOF (HKUST-1) releases $Cu^{2+}$ ions due to dissolution of the MOF, most rapidly in cell culture media. Complete structural collapse is observed within 30 min of HKUST-1 submersion in water. Herein, the materials retain crystallinity after 1 hour of submersion in NBM. In addition, the materials continue to release $Cu^{2+}$ ions beyond the 24 hours tested. Retention of crystallinity may directly enhance the overall efficacy of using a MOF for antibacterial applications. The direct interaction of marine bacterium with copper-MOF surfaces has been reported to lead to the decomposition of SURMOF crystallinity and release of $Cu^{2+}$ ions. Taken together, the data suggests that the particular solid support to which the MOF is bound, the MOF growth process, and PSM may all contribute to the stability and overall copper releasing activity observed with the materials and therefore should be carefully considered for the desired application. Since the $Cu^{2+}$ ions are reportedly toxic to microorganisms including bacteria, $Cu_3(NH_2BTC)_2$-cotton materials warrant further investigation of antimicrobial efficacy.

Example 12: Bacteria Studies

Antibacterial efficacy of the MOF-cotton materials was evaluated against *E. coli* using a standard broth dilution agar plating method. Stock cultures of *E. coli* were obtained by first streaking onto agar plates and placing in a 37° C. incubator until formation of colony-forming units (CFUs). A colony was removed from the agar plate, placed in NBM, and allowed to grow at 37° C. under shaking conditions until reaching an O.D.600 nm~1.0.

Aliquots of the culture were mixed with 30% (v/v) glycerol solution in a 1:1 fashion before being stored at −80° C. until use for future bacteria studies. To perform the antibacterial kill rate studies, the stock culture was thawed on benchtop and subsequently centrifuged at 4700 rpm for 10 min. The supernatant was discarded and the remaining pellet was resuspended using 5 mL warmed NBM. An additional 45 mL NBM was added to the culture and placed under incubated and shaking conditions overnight, until reaching an O.D.600 nm ~1.0.

Example 13: Antibacterial Activity Under Wet Conditions

After overnight growth of the stock culture, the *E. coli* solution was diluted using NBM to a working concentration associated with an O.D.600 nm ~0.35. The cotton materials were placed in a 24-well plate before the addition of 1 mL of the diluted *E. coli* culture. The well plate was placed in a 37° C. incubator and 100 µL aliquots were pulled from each well at 1, 6, and 24 h after exposure to the cotton materials. At each time point, the aliquots underwent 10-fold serial dilutions using 0.85% NaCl solution and subsequently plated on agar using 50 µL. At the end of the total 24 h exposure period, all remaining solution was removed, the wells were washed once with warmed NBM, all swatches were moved to a new well, and 1 mL NBM was added. The plate was sonicated for 5 min (100 W power, 42 kHz frequency) to liberate any bacteria that were adhered to the cotton materials. Aliquots were then taken from the sonicated wells and plated on agar following the above protocol. The agar plates were placed in a 37° C. incubator and CFUs were counted the following day. The assessed CFUs were normalized by the dilution factor and volume by Equation 1. All kill rates by the MOF-cotton swatches are relative to clean natural cotton swatches without MOF present.

$$\frac{CFU}{mL} = \frac{\text{No. of } CFUs}{(\text{Dilution Factor}) * (\text{Vol. Plated})} \quad \text{Equation 1}$$

Given the application of cotton swatches acting as wound dressings, it is useful to determine the remaining cellular viability after exposure to the cotton at varying time points as it has been shown that the relative amount of bacteria present at a wound site is directly attributable to the potential to alter the normal wound healing process. Therefore, the remaining viable *E. coli* cells were assessed after 1, 6, and 24 h exposure to the cotton swatches. Indeed, 6 h is considered the ideal time necessary for bacteria to colonize a wound, however it is also necessary to test the cellular viability after 24 h to ensure no regrowth of the bacteria has occurred. This is considered "wet" experimental conditions, as the materials are fully submerged in the bacteria solution for the entire challenge period. Additionally, both the planktonic (in solution) bacteria were assessed as well as the viable bacteria that attached to the cotton swatches after the 24 h exposure period. This gives insight into both the antibacterial efficacy of the $Cu^{2+}$ ions being released from the MOF-cotton swatches and the ability for the MOF-cotton swatches to impede bacterial attachment and act as an antibacterial surface.

Figure 17:
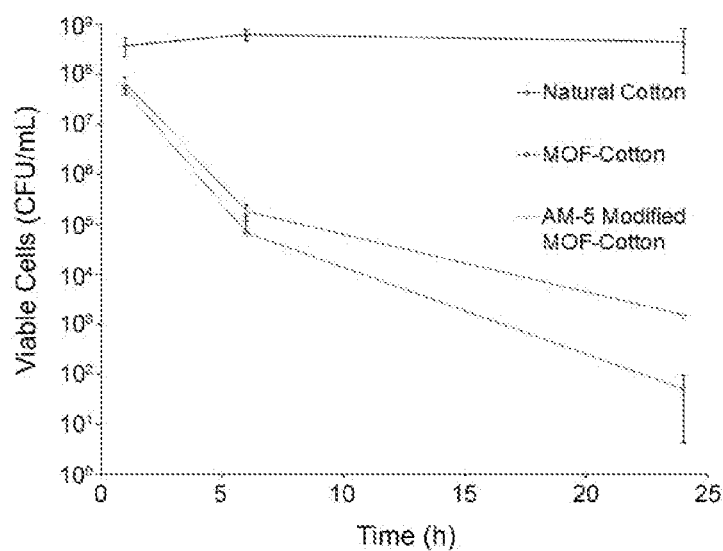
FIG. 17 shows the results from the *E. coli* kill rate study over a 24 hour period.

FIG. 17 shows the results from the E. coli kill rate study over the entire 24 h challenge period. The results show that the cotton swatches alone have no effect on the cellular viability of E. coli at any tested point. Indeed, the E. coli cells assessed in the presence of both the cotton and carboxymethylated cotton swatches were not statistically different when compared to E. coli without any cotton present. As an additional control, the cellular viability of E. coli in the presence of the ligand was assessed (at equal amounts that are present on MOF-cotton swatches) and demonstrated very little antibacterial effect (10' CFUs/mL after 24 h exposure). After the initial h of exposure to the MOF-cotton swatches, there does not appear to be any significant decrease in viability. However, after 6 h of exposure to both the unmodified and modified MOF-cotton swatches, a decrease in planktonic viability is apparent. Both MOF grown surfaces result in a log-3 reduction in cellular viability when compared to the cotton swatch alone. This is a substantial reduction to achieve given the current industry standard is considered a log-3 reduction (equivalent to 99.9% reduction in viable cells). After 24 h of exposure, the reduction in viability is even greater, resulting in a log-4 for the modified MOF and log-5 for the unmodified MOF. This assessment after 24 h is critical as reports have shown significant regrowth of bacteria after initial efficacy was determined.

In addition to the planktonic kill rate achieved using both the modified and unmodified MOF surfaces, the bacterial attachment onto the cotton was depleted in the presence of the MOF-cotton swatches when compared with cotton on its own. FIG. 17 shows the results of this study, where there is a massive log-3 reduction in viable bacteria attached to the MOF-surfaces compared to the cotton surface. Bacterial attachment is the first step in biofilm formation and thus becomes the critical step to ensuring this detrimental effect does not occur. The observed reduction in attachment after 24 h indicates that these materials could indeed act as antibacterial surfaces, particularly through additional tuning of $Cu^{2+}$ ion release to increase the reduction in attachment. It is also interesting to note that there is no statistical difference between the reduction in attachment between the modified and unmodified MOF, given their unique behavior against planktonic bacteria. This would suggest that the remaining MOF (and subsequent copper) that is still present on both types of MOF-swatches is within the threshold to elicit these impressive effects.

Example 14: Antibacterial Activity Under Dry Conditions

The overnight stock culture of E. coli (O.D.600 nm~1.0) was used to assess bacterial attachment onto the cotton swatches under dry conditions. The three types of swatches were placed in a 24-well plate and 10 μL aliquot of the concentrated bacterial solution was added to each swatch. The plate was placed in a 37° C. incubator for 5 min before being assessed for bacterial attachment. The plate was removed after the 5 min exposure period, 1 mL of warmed NBM added, and the plate was sonicated for 5 min. Viable bacteria were plated for CFUs and assessed via Equation 1.

Figure 18:
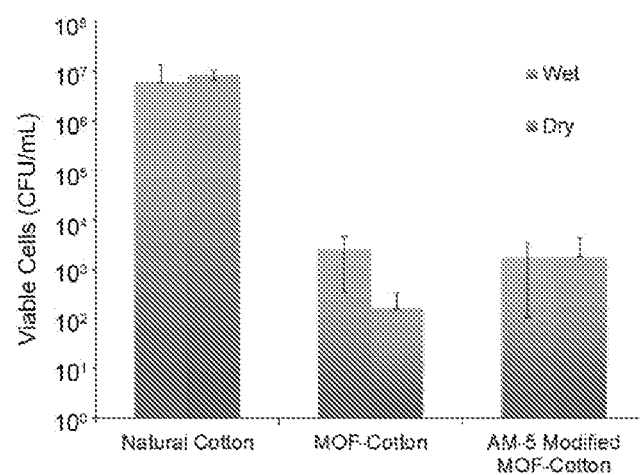
FIG. 18 is a graph of results of a bacterial study under wet conditions and dry conditions.

To understand how these materials behave as antibacterial surfaces under circumstances more similar to a pure copper surface application, dry conditions were also employed. This examines the efficacy of the materials without a direct contribution to metal ions releasing into solution and killing planktonic bacteria. This method is also more representative of the wound healing model, where there is not a continuous solution of bacteria surrounding the materials. A 5 min exposure period was chosen based off previous bacteria studies using metal surfaces. The results from this study (and the wet attachment study) are shown in FIG. 18, in which results from the wet conditions are shown on the left and dry conditions on the right. As shown, there is a further enhanced reduction in attachment onto the unmodified swatches under dry conditions then what was observed under wet conditions (log-4 versus log-3), and a similar reduction in attachment observed for the modified swatch. This is a remarkable reduction in attachment to achieve using a minimal 5 min exposure period. This indicates that the inability for E. coli cells to begin the biofilm process is near immediate, representing an attractive option for biofilm impediment. It is also fascinating that the total amount of attached cells onto the natural cotton is the same, regardless of exposure time or wet versus dry conditions.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The following is claimed:

1. A method of forming a modified textile, the method comprising:
   carboxymethylation of a surface of a textile;
   layer-by-layer growth of a copper tricarboxylate metal-organic framework film on the surface of the carboxymethylated surface;
   selecting an anhydride that will confer hydrophobicity to the copper tricarboxylate metal-organic framework film, wherein the anhydride is valeric anhydride; and
   forming a modified tricarboxylate metal-organic framework film by exposing the copper tricarboxylate metal-organic framework film to a determined effective amount of the valeric anhydride to produce a hydrophobic textile having a determined characteristic, wherein the determined characteristic is one of water contact angle, water stability, and degradation rate of the tricarboxylate metal-organic framework.

2. The method of claim 1 wherein carboxymethylation includes exposing the surface of the textile to a solvent comprising water and an alcohol.

3. The method of claim 1 wherein the ligand solution includes 2-aminobenzene-1,3,5-tricarboxylic acid.

4. The method of claim 1 wherein the determined characteristic is water stability and the hydrophobic textile is stable in water for at least 30 minutes.

* * * * *